United States Patent
Hester et al.

(10) Patent No.: US 10,722,848 B2
(45) Date of Patent: Jul. 28, 2020

(54) FILTRATION MEDIUM SEQUENCE FOR BIOMATERIAL PURIFICATION

(71) Applicant: 3M INNOVATIVE PROPERTIES COMPANY, St. Paul, MN (US)

(72) Inventors: Jonathan F. Hester, Hudson, WI (US); Angelines A. Castro Forero, Hudson, WI (US); Gregory M. Jellum, Marine on St. Croix, MN (US); Jerald K. Rasmussen, Woodville, WI (US); Kannan Seshadri, Woodbury, MN (US); Clinton P. Waller, Jr., White Bear Lake, MN (US)

(73) Assignee: 3M Innovative Properties Company, St. Paul, MN (US)

( * ) Notice: Subject to any disclaimer, the term of this patent is extended or adjusted under 35 U.S.C. 154(b) by 131 days.

(21) Appl. No.: 15/755,584

(22) PCT Filed: Oct. 11, 2016

(86) PCT No.: PCT/US2016/056326
§ 371 (c)(1),
(2) Date: Feb. 27, 2018

(87) PCT Pub. No.: WO2017/069965
PCT Pub. Date: Apr. 27, 2017

(65) Prior Publication Data
US 2018/0257042 A1    Sep. 13, 2018

Related U.S. Application Data

(60) Provisional application No. 62/245,403, filed on Oct. 23, 2015.

(51) Int. Cl.
*B01D 69/12* (2006.01)
*B01D 67/00* (2006.01)
(Continued)

(52) U.S. Cl.
CPC ........... *B01D 69/125* (2013.01); *B01D 63/10* (2013.01); *B01D 63/14* (2013.01); *B01D 67/009* (2013.01);
(Continued)

(58) Field of Classification Search
CPC ........ B01D 69/12; B01D 69/10; B01D 71/40; B01D 71/78
See application file for complete search history.

(56) References Cited

U.S. PATENT DOCUMENTS 3,876,738 A    4/1975  Marinaccio
3,928,517 A   12/1975  Knight
(Continued)

FOREIGN PATENT DOCUMENTS

JP         47-40913    10/1972
RU         2131284      6/1999
(Continued)

OTHER PUBLICATIONS

Castro-Forero, "Anion-Exchange Chromatographic Clarification Bringing Simplification, Robustness, and Savings to MAb Purifications", BioProcess International, Jun. 2015, vol. 13, No. 6, pp. 52-57.
(Continued)

*Primary Examiner* — Ellen M McAvoy
(74) *Attorney, Agent, or Firm* — Julie Lapos-Kuchar

(57) ABSTRACT

Described herein is a filtration media comprising: (i) a first filtration medium comprising an anion exchange nonwoven substrate, wherein the anion exchange nonwoven substrate comprises a plurality of quaternary ammonium groups; and (ii) a second filtration medium comprising a functionalized microporous membrane wherein the functionalized microporous membrane comprises a plurality of guanidyl groups; wherein the first filtration medium is positioned upstream of the second filtration medium.

20 Claims, 5 Drawing Sheets

(51) Int. Cl.
- *B01D 71/40* (2006.01)
- *B01D 71/78* (2006.01)
- *B01D 69/10* (2006.01)
- *B01D 63/10* (2006.01)
- *B01D 63/14* (2006.01)
- *B01D 69/02* (2006.01)
- *C07K 1/34* (2006.01)

(52) U.S. Cl.
CPC ......... *B01D 67/0093* (2013.01); *B01D 69/02* (2013.01); *B01D 69/10* (2013.01); *B01D 71/40* (2013.01); *B01D 71/78* (2013.01); *C07K 1/34* (2013.01); *B01D 2323/16* (2013.01); *B01D 2323/345* (2013.01); *B01D 2323/38* (2013.01); *B01D 2323/385* (2013.01); *B01D 2323/42* (2013.01); *B01D 2325/16* (2013.01); *B01D 2325/42* (2013.01)

(56) References Cited

U.S. PATENT DOCUMENTS

| | | | |
|---|---|---|---|
| 4,118,531 A | 10/1978 | Hauser | |
| 4,529,256 A | 7/1985 | Kretzschmar | |
| 4,707,265 A | 11/1987 | Barnes, Jr. | |
| 4,726,989 A | 2/1988 | Mrozinski | |
| 4,867,881 A | 9/1989 | Kinzer | |
| 5,120,594 A | 6/1992 | Mrozinski | |
| 5,260,360 A | 11/1993 | Mrozinski | |
| 5,458,782 A | 10/1995 | Hou | |
| 5,522,997 A | 6/1996 | Virnig | |
| 5,567,615 A | 10/1996 | Degen | |
| 5,962,544 A | 10/1999 | Waller, Jr. | |
| 6,056,529 A | 5/2000 | Meyering | |
| 6,267,916 B1 | 7/2001 | Meyering | |
| 6,315,130 B1 | 11/2001 | Olsen | |
| 6,413,070 B1 | 7/2002 | Meyering | |
| 6,464,084 B2 | 10/2002 | Pulek | |
| 6,521,011 B1 | 2/2003 | Sundet | |
| 6,712,966 B1 | 3/2004 | Pulek | |
| 6,776,940 B2 | 8/2004 | Meyering | |
| 6,780,327 B1 | 8/2004 | Wu | |
| 6,939,466 B2 | 9/2005 | Pulek | |
| 7,094,347 B2 | 8/2006 | Wu | |
| 7,178,676 B2 | 2/2007 | Pulek | |
| 7,338,692 B2 | 3/2008 | Smith | |
| 8,328,023 B2 | 12/2012 | Weiss | |
| 8,459,470 B2 | 6/2013 | Weiss | |
| 8,551,894 B2 | 10/2013 | Seshadri | |
| 8,586,338 B2 | 11/2013 | Etzel | |
| 8,652,582 B2 | 2/2014 | Bothof | |
| 8,846,203 B2 | 9/2014 | Bothof | |
| 9,821,276 B2 * | 11/2017 | Berrigan | B01D 67/0093 |
| 2010/0155323 A1 | 6/2010 | Weiss | |
| 2010/0210160 A1 | 8/2010 | Hester | |
| 2011/0033633 A1 | 2/2011 | Bothof | |
| 2011/0207196 A1 | 8/2011 | Koehler | |
| 2011/0259812 A1 | 10/2011 | Marks | |
| 2011/0297604 A1 | 12/2011 | Bryan | |
| 2012/0252091 A1 | 10/2012 | Rasmussen | |
| 2014/0364519 A1 | 12/2014 | Bothof | |
| 2015/0099413 A1 | 4/2015 | Berrigan | |
| 2015/0136698 A1 | 5/2015 | Bothof | |
| 2015/0203645 A1 | 6/2015 | Rasmussen | |
| 2018/0188230 A1 * | 7/2018 | Huff | G01N 33/48721 |

FOREIGN PATENT DOCUMENTS

| | | |
|---|---|---|
| RU | 2170136 | 7/2001 |
| WO | WO 2009-148869 | 12/2009 |
| WO | WO 2013-162695 | 10/2013 |

OTHER PUBLICATIONS

Davies, "The Separation of Airborne Dust and Particles," Institution of Mechanical Engineers, London, Proceedings 1B, 1952, pp. 185-213.

Wente, "Manufacture of Superfine Organic Fibers", Naval Research Laboratories Report No. 4364, 1954, 24pgs.

International Search Report for PCT International Application No. PCT/US2016/056326, dated Jan. 4, 2017, 5pgs.

* cited by examiner

FILTRATION MEDIUM SEQUENCE FOR BIOMATERIAL PURIFICATION

CROSS REFERENCE TO RELATED APPLICATIONS

This application is a national stage filing under 35 U.S.C. 371 of PCT/US2016/056326, filed Oct. 11, 2016, which claims the benefit of U.S. Application No. 62/245,403, filed Oct. 23, 2015, the disclosure of which is incorporated by reference in its/their entirety herein.

TECHNICAL FIELD

A filtration medium sequence comprising a functionalized nonwoven and a functionalized porous membrane is disclosed. The filtration medium sequence is useful, for example, in biomaterial purification.

BACKGROUND

Manufacturing of large scale or commercial quantities of therapeutically useful targeted biomaterials, such as proteins, can be accomplished by growing cells that are engineered to produce a desired protein in bioreactors under controlled conditions. The technology used involves, for example, the fermentation of microorganisms which have been altered through recombinant DNA techniques or the culturing of mammalian cells which have been altered through hybridoma techniques. The cells are suspended in a broth which contains the salts, sugars, proteins, and various factors necessary to support the growth of particular cells. The desired product may be either secreted by the cells into the broth or retained within the cell body. The harvested broth is then processed to recover, purify, and concentrate the desired product.

The separation, or purification, of these targeted biomaterials from a heterogeneous mixture has proven to be a formidable task for at least the following reasons: the desired product often represents a small percentage of total cell culture fluid, which comprises significant quantities of particulate and soluble contaminants, and the cell culture fluid can comprise high salt concentrations.

As a result of these factors, extensive downstream processing has been necessarily used to yield high quantities of purified product. Such downstream processing includes the many stages of processing that take place subsequent to the production of the targeted biomaterial including, for example, centrifugation, cell disruption, mechanical sieving, microfiltration, ion-exchange, cross-flow filtration, affinity separation, sterilization, purification, and packaging. The downstream processing represents a major cost in the production of bioprocessed products.

Various filtration articles have been described for the purification or separation of targeted biomaterials from fluid mixtures. U.S. Pat. Publ. No. 2011/0207196 (Koehler et al.) describes a depth filter layer with an inorganic double hydroxide layer for retaining contaminants such as DNA, while proteins of biotechnological processes are transmissible therethrough. U.S. Pat. No. 5,567,615 (Degen et al.) describes an affinity separation method involving dynamic filtration said to be particularly useful in the isolation of biologically active compounds. U.S. Pat. Publ. No. 2012/0252091 (Rasmussen et al.) describes a substrate grafted with a polymer that has affinity for binding neutral or negatively charged biomaterials.

SUMMARY

There is a desire for filtration media to increase the cost efficiency of isolation and/or purification of biomaterials from fluid samples. Such efficiency may be in the form of increased throughput, due to the reduction of process steps, increased throughput of a single step, and/or better removal of contaminants resulting in reduced loading of impurities onto downstream purification devices (such as chromatography columns or filters).

In one aspect, a filtration medium sequence is described comprising:
  (i) a first filtration medium comprising an anion exchange nonwoven substrate, wherein the anion exchange nonwoven substrate comprises a plurality of quaternary ammonium groups; and
  (ii) a second filtration medium comprising a functionalized microporous membrane wherein the functionalized microporous membrane comprises a plurality of guanidyl groups;
wherein the first filtration medium is positioned upstream of the second filtration medium.

In another aspect, a method of filtration of a biological fluid is described comprising:
  (a) providing the biological fluid, wherein the biological fluid comprises a targeted biomaterial and contaminants, and
  (b) contacting the biological fluid with a filtration medium sequence, the filtration medium sequence comprising:
    (i) a first filtration medium comprising an anion exchange nonwoven substrate, wherein the anion exchange nonwoven substrate comprises a plurality of quaternary ammonium groups; and (ii) a second filtration medium comprising a functionalized microporous membrane wherein the functionalized microporous membrane comprises a plurality of guanidyl groups; and wherein the first filtration medium is positioned upstream of the second filtration medium.

The above summary is not intended to describe each embodiment. The details of one or more embodiments of the invention are also set forth in the description below. Other features, objects, and advantages will be apparent from the description and from the claims.

Figure 1:
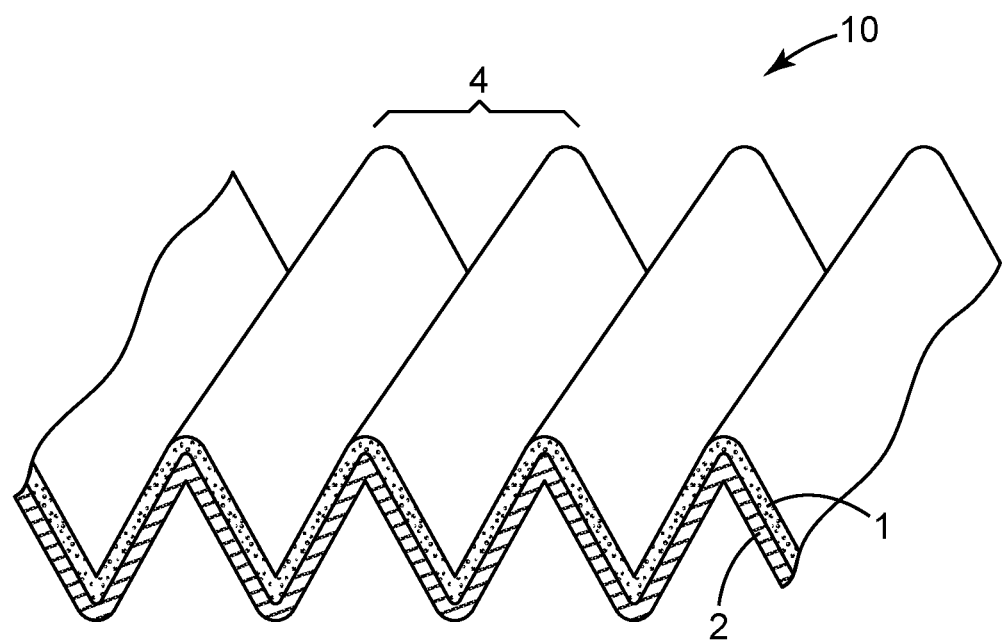
FIG. 1 is a perspective view of an exemplary embodiment of a filtration medium sequence according to the present disclosure formed into a multilayered article comprising a plurality of pleats.

While the above-identified FIGS. 1-5 set forth several embodiments of the present disclosure, other embodiments are also contemplated, as noted in the discussion. In all cases, this disclosure presents the disclosure by way of representation and not limitations.

DETAILED DESCRIPTION

As used herein, the term

"Alkyl" means a linear or branched, cyclic or acyclic, saturated monovalent hydrocarbon having from one to about twelve carbon atoms, e.g., methyl, ethyl, 1-propyl, 2-propyl, pentyl, and the like.

"Alkylene" means a linear saturated divalent hydrocarbon having from one to about twelve carbon atoms or a branched saturated divalent hydrocarbon having from three to about twelve carbon atoms, e.g., methylene, ethylene, propylene, 2-methylpropylene, pentylene, hexylene, and the like.

"Alkenyl" means a linear unsaturated monovalent hydrocarbon having from two to about twelve carbon atoms or a branched unsaturated hydrocarbon having from three to about twelve carbon atoms.

"Alkenoyl" means an alkenyl group that comprises a carbonyl (—C(=O)—) group.

"Aryl" means a monovalent aromatic, such as phenyl, naphthyl and the like.

"Guanidyl" means a functional group selected from at least one of guanidine and biguanide.

"Heteroarylene" refers to a divalent group that is aromatic and heterocyclic. That is, the heteroarylene includes at least one heteroatom in an aromatic ring having 5 or 6 members. Suitable heteroatoms are typically oxy, thio, or amino. The group can have one to five rings that are connected, fused, or a combination thereof. At least one ring is heteroaromatic and any other ring can be aromatic, non-aromatic, heterocyclic, carbocyclic, or a combination thereof. In some embodiments, the heteroarylene has up to 5 rings, up to 4 rings, up to 3 rings, up to 2 rings, or one ring. Examples of heteroarylene groups include, but are not limited to, triazinediyl, pyridine-diyl, pyrimidine-diyl, pyridazine-diyl, and the like.

"hydrocarbyl" is inclusive of aryl and alkyl;

"(Hetero)hydrocarbyl" is inclusive of hydrocarbyl alkyl and aryl groups, and heterohydrocarbyl heteroalkyl and heteroaryl groups, the later comprising one or more catenary (in-chain) heteroatoms such as oxygen or nitrogen atoms. Heterohydrocarbyl may optionally contain one or more catenary (in-chain) functional groups including ester, amide, urea, urethane, and carbonate functional groups. Unless otherwise indicated, the non-polymeric (hetero)hydrocarbyl groups typically contain from 1 to 60 carbon atoms. Some examples of such heterohydrocarbyls as used herein include, but are not limited to, methoxy, ethoxy, propoxy, 4-diphenylaminobutyl, 2-(2'-phenoxyethoxy)ethyl, 3,6-dioxaheptyl, 3,6-dioxahexyl-6-phenyl, in addition to those described for "alkyl", "heteroalkyl", "aryl", and "heteroaryl" supra.

"a", "an", and "the" are used interchangeably and mean one or more.

"and/or" is used to indicate one or both stated cases may occur, for example A and/or B includes, (A and B) and (A or B).

Also herein, recitation of ranges by endpoints includes all numbers subsumed within that range (e.g., 1 to 10 includes 1.4, 1.9, 2.33, 5.75, 9.98, etc.).

Also herein, recitation of "at least one" includes all numbers of one and greater (e.g., at least 2, at least 4, at least 6, at least 8, at least 10, at least 25, at least 50, at least 100, etc.).

The present disclosure provides a filtration medium sequence comprising two different substrates functionalized with different functionalized ligands. The filtration medium sequence comprises at least two different functionalized media in a particular order. In one embodiment, (i) a first filtration medium which comprises a nonwoven substrate functionalized with quaternary ammonium groups is located upstream of (ii) a second filtration medium which comprises a microporous membrane substrate functionalized with guanidyl groups.

The first filtration medium (i) is an anion exchange nonwoven substrate comprising quaternary ammonium groups.

The nonwoven substrate is a nonwoven web which may include nonwoven webs manufactured by any of the commonly known processes for producing nonwoven webs. As used herein, the term "nonwoven web" refers to a fabric that has a structure of individual fibers or filaments which are randomly and/or unidirectionally interlaid in a mat-like fashion.

For example, the fibrous nonwoven web can be made by carded, air laid, wet laid, spunlaced, spunbonding, electrospinning or melt-blowing techniques, such as melt-spun or meltblown, or combinations thereof. Spunbonded fibers are typically small diameter fibers that are formed by extruding molten thermoplastic polymer as filaments from a plurality of fine, usually circular capillaries of a spinneret with the diameter of the extruded fibers being rapidly reduced. Meltblown fibers are typically formed by extruding the molten thermoplastic material through a plurality of fine, usually circular, die capillaries as molten threads or filaments into a high velocity, usually heated gas (e.g. air) stream which attenuates the filaments of molten thermoplastic material to reduce their diameter. Thereafter, the meltblown fibers are carried by the high velocity gas stream and are deposited on a collecting surface to from a web of randomly disbursed meltblown fibers. Any of the non-woven webs may be made from a single type of fiber or two or more fibers that differ in the type of thermoplastic polymer and/or thickness.

Staple fibers may also be present in the web. The presence of staple fibers generally provides a loftier, less dense web than a web of only melt blown microfibers. Preferably, no more than about 20 weight percent staple fibers are present, more preferably no more than about 10 weight percent. Such webs containing staple fiber are disclosed in U.S. Pat. No. 4,118,531 (Hauser).

The nonwoven article may optionally further comprise one or more layers of scrim. For example, either or both major surfaces may each optionally further comprise a scrim layer. The scrim, which is typically a woven or nonwoven reinforcement made from fibers, is included to provide strength to the nonwoven article. Suitable scrim materials include, but are not limited to, nylon, polyester, fiberglass, polyethylene, polypropylene, and the like. The average thickness of the scrim can vary. Typically, the average thickness of the scrim ranges from about 25 to about 100 micrometers, preferably about 25 to about 50 micrometers. The layer of the scrim may optionally be bonded to the nonwoven article. A variety of adhesive materials can be used to bond the scrim to the polymeric material. Alternatively, the scrim may be heat-bonded to the nonwoven.

The microfibers of the nonwoven substrate typically have an effective fiber diameter of from at least 0.5, 1, 2, or even 4 micrometers and at most 15, 10, 8, or even 6 micrometers, as calculated according to the method set forth in Davies, C. N., "The Separation of Airborne Dust and Particles," Institution of Mechanical Engineers, London, Proceedings 1B, 1952. The nonwoven substrate preferably has a basis weight in the range of at least 5, 10, 20, or even 50 g/m$^2$; and at most 800, 600, 400, 200, or even 100 g/m$^2$. The minimum tensile strength of the nonwoven web is about 4.0 Newtons. It is generally recognized that the tensile strength of nonwovens is lower in the machine direction than in the cross-web direction due to better fiber bonding and entanglement in the latter.

Further details on the manufacturing method of nonwoven webs may be found in Wente, Superfine Thermoplastic Fibers, 48 INDUS. ENG. CHEM. 1342 (1956), or in Wente et al., Manufacture Of Superfine Organic Fibers (Naval Research Laboratories Report No. 4364, 1954).

Nonwoven web loft is measured by solidity, a parameter that defines the solids fraction in a volume of web. Lower solidity values are indicative of greater web loft. Useful nonwoven substrates have a solidity of less than 20% or even less than 15%. Solidity is a unitless fraction typically represented by α:

$$\alpha = m_f \div \rho_f \times L_{nonwoven}$$

where $m_f$ is the fiber mass per sample surface area, which $\rho_f$ is the fiber density; and $L_{nonwoven}$ is the nonwoven thickness. Solidity is used herein to refer to the nonwoven substrate itself and not to the functionalized nonwoven. When a nonwoven substrate contains mixtures of two or more kinds of fibers, the individual solidities are determined for each kind of fiber using the same $L_{nonwoven}$ and these individual solidities are added together to obtain the web's solidity, α.

The nonwoven substrate may be formed from fibers or filaments made of any suitable thermoplastic polymeric material. Suitable polymeric materials include, but are not limited to, polyolefins, poly(isoprenes), poly(butadienes), fluorinated polymers, chlorinated polymers, polyamides, polyimides, polyethers, poly(ether sulfones), poly(sulfones), poly(vinyl acetates), copolymers of vinyl acetate, such as poly(ethylene)-co-poly(vinyl alcohol), poly(phosphazenes), poly(vinyl esters), poly(vinyl ethers), poly(vinyl alcohols), and poly(carbonates).

Suitable polyolefins include, but are not limited to, poly(ethylene), poly(propylene), poly(1-butene), copolymers of ethylene and propylene, alpha olefin copolymers (such as copolymers of ethylene or propylene with 1-butene, 1-hexene, 1-octene, and 1-decene), poly(ethylene-co-1-butene) and poly(ethylene-co-1-butene-co-1-hexene).

Suitable fluorinated polymers include, but are not limited to, poly(vinyl fluoride), poly(vinylidene fluoride), copolymers of vinylidene fluoride (such as poly(vinylidene fluoride-co-hexafluoropropylene), and copolymers of chlorotrifluoroethylene (such as poly(ethylene-co-chlorotrifluoroethylene).

Suitable polyamides include, but are not limited to: poly(iminoadipoyliminohexamethylene), poly(iminoadipoyliminodecamethylene), and polycaprolactam. Suitable polyimides include poly(pyromellitimide).

Suitable poly(ether sulfones) include, but are not limited to, poly(diphenylether sulfone) and poly(diphenylsulfone-co-diphenylene oxide sulfone).

Suitable copolymers of vinyl acetate include, but are not limited to, poly(ethylene-co-vinyl acetate) and such copolymers in which at least some of the acetate groups have been hydrolyzed to afford various poly(vinyl alcohols) including, poly(ethylene-co-vinyl alcohol).

The nonwoven substrate of the present disclosure is treated to comprise a quaternary ammonium functional group, i.e., —N$^+$ R$^1$R$^2$R$^3$X$^-$ where X$^-$ is a counter ion group, often a halide (e.g., Cl$^-$), a sulfate, a phosphate, a nitrate, and the like. In some embodiments, R$^1$, R$^2$, and R$^3$ of the ammonium functional group are all methyl. In other embodiments, one of the R$^1$, R$^2$, or R$^3$ groups is methyl and the other two are an alkyl having 2 to 18, 2 to 10, 2 to 6, or 2 to 4 carbon atoms. In other embodiments, two of the R$^1$, R$^2$, or R$^3$ groups are methyl and the other group is an alkyl having 2 to 18, 2 to 10, 2 to 6, or 2 to 4 carbon atoms. In yet other embodiments, at least two of the R$^1$, R$^2$, and R$^3$ groups combine with the nitrogen atom to which they are attached to form a heterocyclic group. The heterocyclic group includes at least one nitrogen atom and can contain other heteroatoms such as oxygen or sulfur. Exemplary heterocyclic groups include, but are not limited to piperidinyl and morpholinyl. The heterocyclic group can be fused to an additional ring such as a benzene, cyclohexene, or cyclohexane.

The quaternary ammonium group is covalently bonded to the nonwoven substrate using techniques known in the art. Typically, the quaternary ammonium group is grafted via a linking group directly onto the nonwoven substrate or onto a nonwoven substrate that has been treated with a primer layer.

In one embodiment, the nonwoven substrate is grafted using a quaternary ammonium salt of an aminoalkyl(meth)acryloyl monomer such as

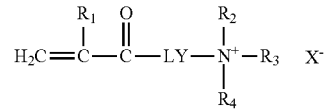

Formula I

Where $R_1$ is hydrogen or methyl, preferably methyl; L is —O— or —NH—; and Y is an alkylene (e.g., an alkylene having 2 to 10 carbon atoms, 2 to 6, or 2 to 4 carbon atoms). $R_2$, $R_3$, and $R_4$, are independently aryl or alkyl, preferably $C_1$-$C_4$ alkyl; and X$^-$ is the counter anion.

Exemplary quaternary salts of the aminoalkyl (meth)acryloyl monomers of Formula I include, but are not limited to, (meth)acrylamidoalkyltrimethylammonium salts (e.g., 3-methacrylamidopropyltrimethylammonium chloride and 3-acrylamidopropyltrimethylammonium chloride) and (meth)acryloxyalkyltrimethylammonium salts (e.g., 2-acryloxyethyltrimethylammonium chloride, 2-methacryloxyethyltrimethylammonium chloride, 3-methacryloxy-2-hydroxypropyltrimethylammonium chloride, 3-acryloxy-2-hydroxypropyltrimethylammonium chloride, and 2-acryloxyethyltrimethylammonium methyl sulfate).

Such monomers having a quaternary ammonium group of Formula I may be directly grafted to the surface of the nonwoven substrate or a grafting aminoalkyl (meth)acryloyl monomer, having a primary, secondary or tertiary amine group, may be grafted and subsequently converted to a quaternary ammonium group by alkylation. Such manufacture of anion exchange nonwovens is described in U.S. Pat. No. 8,328,023 (Weiss et al.).

In one embodiment, the grafted polymer having quaternary ammonium groups derived from the monomer of Formula I further comprises units derived from monofunctional ethylenically-unsaturated monomers having a poly(alkylene oxide) group. The monomer units having a poly(alkylene oxide) group is of the formula:
$Z\text{-}Q\text{-}(CH(R^5)\text{—}CH_2\text{—}O)_m\text{—}R^6$, wherein Z is a polymerizable ethylenically unsaturated moiety, $R^5$ is a H or a $C_1$ to $C_4$ alkyl group; Q is $N(R^5)$ or O; and $R^6$ is a H, a $C_1$ to $C_4$ alkyl group, aryl group, or combinations thereof and m is from 2 to 100, preferably 5 to 20. Useful ethylenically unsaturated moiety, Z, of the monomer may include:

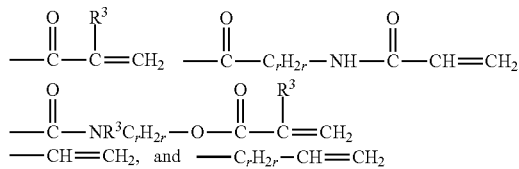

wherein $R^3$ is H or —$CH_3$ and r=1-10.

Examples of suitable monofunctional poly(alkylene oxide) monomers include poly(ethylene oxide) (meth)acrylate, poly(propylene oxide) (meth)acrylate, poly(ethylene oxide-propylene oxide) (meth)acrylate, and combinations thereof. Such monomers preferably include one nonreactive end group such as hydrogen, ($C_1$-$C_4$)alkoxy, aryloxy (e.g., phenoxy), and ($C_1$-$C_4$)alkaryloxy. These groups can be linear or branched. These monomers can be of a wide range of molecular weights and are commercially available from sources such as Sartomer Company, Exton, Pa.; Shinnakamura Chemical Co., Ltd., Tokyo, Japan; Aldrich, Milwaukee, Wis.; and Osaka Organic Chemical Ind., Ltd., Osaka, Japan.

In one embodiment, the grafted polymers comprising the quaternary ammonium group of Formula I are further derived from "hydrophilic monomers". As used herein "hydrophilic monomers" are those polymerizable monomers having a water miscibility (water in monomer) of at least 1 wt. %, preferably at least 5 weight % without reaching a cloud point, are exclusive of poly(alkylene oxide) monomers and contain no acidic functional groups or groups that would retard the grafting polymerization. Examples of suitable hydrophilic monomers include 2-hydroxyethyl(meth)acrylate (HEMA), 2-hydroxypropyl(meth)acrylate, 3-hydroxypropyl(meth)acrylate, 2,3-dihydroxypropyl (meth)acrylate, 4-hydroxybutyl(meth)acrylate, N-vinyl caprolactam, N-vinyl acetamide, N-vinyl pyrrolidone, acrylonitrile, tetrahydrofurfuryl acrylate, acrylamide, mono- or di-N-alkyl substituted acrylamide, glycerol methacrylate, and combinations thereof. Preferred polar monomers include 2-hydroxyethyl(meth)acrylate (HEMA), N-vinyl pyrrolidone, N-vinyl acetamide, methylacrylamide, and mixtures thereof. In one embodiment, the grafted polymers comprising the quaternary ammonium group of Formula I is a polymer derived from aminoalkyl (meth)acryloyl monomer, poly(alkylene oxide) monomer and optionally a second hydrophilic monomer. In one embodiment the grafted polymer is derived from 80 to 98 wt. % of an aminoalkyl (meth)acryloyl monomer: 2 to 20 wt. % of a poly(alkylene oxide) monomer; and 0 to 10 wt. % of the hydrophilic monomer. Examples of suitable poly(alkylene oxide) monomers include poly(ethylene oxide) (meth)acrylate, poly(propylene oxide) (meth)acrylate, poly(ethylene oxide-propylene oxide) (meth)acrylate, and combinations thereof. More information regarding such a grafting may be found in U.S. Pat. No. 8,328,023 (Weiss et al.).

In one embodiment, the grafted polymers comprising the quaternary ammonium group of Formula I are further derived from an amide monomer, an oxy monomer and optionally a poly(alkylene oxide) monomer. In one embodiment the grafted polymer is derived from 10 to 50 parts by weight of a quaternary ammonium group comprising monomer; 10 to 80 parts by weight of an amide monomer: 10 to 40 parts by weight of an oxy monomer; and 0 to 30 parts by weight of the poly(alkylene oxide) monomer.

The amide monomer is a hydrophilic monomer comprising (meth)acrylamides and N-vinyl amides of the general formulas:

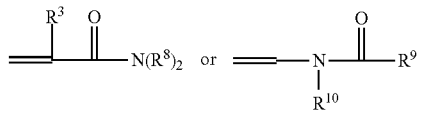

where $R^3$ is —H or $C_1$-$C_4$ alkyl; each $R^8$ is an H, an alkyl or an aryl group, $R^9$ and $R^{10}$ are alkyl groups, or may be taken together to form a 5 or 6-membered ring. Examples of suitable hydrophilic amide monomers include N-vinyl caprolactam, N-vinyl acetamide, N-vinyl pyrrolidone, acrylamide, mono- or di-N-alkyl substituted acrylamide, and combinations thereof. Preferred amide monomers include N-vinyl pyrrolidone, N-vinyl acetamide, methylacrylamide, and mixtures thereof. The oxy monomer includes epoxy-functional and monoether-functional (meth)acrylates and (meth)acrylamides and those of the general formula:

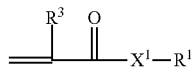

wherein:
$R^3$ is —H or $C_1$-$C_4$ alkyl; $X^1$ is —$NR^3$— or —O—; and $R^1$ is an epoxy-functional or ether-functional (hetero)hydrocarbyl group. More particularly the ether functional group is a lower alkyleneoxy alkyl group. Preferably, the $R^1$ group is based on a straight-chain, branched, cyclic or polycyclic hydrocarbon of 2 to 30 carbons having an oxirane (epoxy) group included. More preferably, the $R^8$ group contains 3 to 10 carbons, such as glycidyl methacrylate (GMA). More information regarding such a grafting may be found in U.S. Pat. Publ. No. 2015/0099413 (Berrigan et al.).

The average thickness of the first filtration medium is preferably at least 0.1, 0.25, or even 1 mm; and at most 5, 8 or even 10 mm.

In one embodiment, the first filtration medium comprises at least 0.1, 0.2, 0.4, 0.8, 1, or even 5 mmol of quaternary ammonium groups per gram of the first filtration medium.

The second filtration medium (ii) is a microporous membrane substrate functionalized with guanidyl groups.

The microporous membrane is a porous polymeric substrate (such as sheet or film) comprising micropores with a mean flow pore size, as characterized by ASTM Standard Test Method No. F316-03, "Standard Test Methods for Pore Size Characteristics of Membrane Filters by Bubble Point and Mean Flow Pore Test," of less than 5 micrometers. In one embodiment, the microporous membrane has a mean flow pore size of at least 0.1, 0.2, 0.5, 0.8, or even 1 micrometer; and at most 5, 3, or even 2 micrometers. The desired pore size may vary depending on the application. The microporous membrane can have a symmetric or asymmetric (e.g., gradient) distribution of pore size in the direction of fluid flow.

The microporous membrane may be formed from any suitable thermoplastic polymeric material. Suitable polymeric materials include, but are not limited to, polyolefins, poly(isoprenes), poly(butadienes), fluorinated polymers, chlorinated polymers, polyamides, polyimides, polyethers, poly(ether sulfones), poly(sulfones), poly(vinyl acetates), polyesters such as poly(lactic acid), copolymers of vinyl acetate, such as poly(ethylene)-co-poly(vinyl alcohol), poly(phosphazenes), poly(vinyl esters), poly(vinyl ethers), poly(vinyl alcohols), and poly(carbonates).

Suitable polyolefins include, but are not limited to, poly(ethylene), poly(propylene), poly(1-butene), copolymers of ethylene and propylene, alpha olefin copolymers (such as copolymers of ethylene or propylene with 1-butene, 1-hexene, 1-octene, and 1-decene), poly(ethylene-co-1-butene) and poly(ethylene-co-1-butene-co-1-hexene).

Suitable fluorinated polymers include, but are not limited to, poly(vinyl fluoride), poly(vinylidene fluoride), copolymers of vinylidene fluoride (such as poly(vinylidene fluoride-co-hexafluoropropylene), and copolymers of chlorotrifluoroethylene (such as poly(ethylene-co-chlorotrifluoroethylene).

Suitable polyamides include, but are not limited to, poly(iminoadipolyliminohexamethylene), poly(iminoadipolyliminodecamethylene), and polycaprolactam. Suitable polyimides include, but are not limited to, poly(pyromellitimide).

Suitable poly(ether sulfones) include, but are not limited to, poly(diphenylether sulfone) and poly(diphenylsulfone-co-diphenylene oxide sulfone).

Suitable copolymers of vinyl acetate include, but are not limited to, poly(ethylene-co-vinyl acetate) and such copolymers in which at least some of the acetate groups have been hydrolyzed to afford various poly(vinyl alcohols).

In one embodiment, the microporous membrane is a solvent-induced phase separation (SIPS) membrane. SIPS membranes are often made by preparing a homogeneous solution of a polymer in first solvent(s), casting the solution into desired shape, e.g. flat sheet or hollow fiber, contacting the cast solution with another second solvent that is a non-solvent for the polymer, but a solvent for the first solvent (i.e., the first solvent is miscible with the second solvent, but the polymer is not). Phase separation is induced by diffusion of the second solvent into the cast polymer solution and diffusion of the first solvent out of the polymer solution and into the second solvent, thus precipitating the polymer. The polymer-lean phase is removed and the polymer is dried to yield the porous structure. SIPS is also called Phase Inversion, or Diffusion-induced Phase Separation, or Nonsolvent-induced Phase Separation, such techniques are commonly known in the art. Microporous SIPS membranes are further disclosed in U.S. Pat. No. 6,056,529 (Meyering et al.), U.S. Pat. No. 6,267,916 (Meyering et al.), U.S. Pat. No. 6,413,070 (Meyering et al.), U.S. Pat. No. 6,776,940 (Meyering et al.), U.S. Pat. No. 3,876,738 (Marinacchio et al.), U.S. Pat. No. 3,928,517 (Knight et al.), U.S. Pat. No. 4,707,265 (Knight et al.), and U.S. Pat. No. 5,458,782 (Hou et al.).

In another embodiment, the microporous membrane is a thermally-induced phase separation (TIPS) membrane. TIPS membranes are often prepared by forming a homogenous solution of a thermoplastic material and a second material (such as a diluent), and optionally including a nucleating agent, by mixing at elevated temperatures in plastic compounding equipment, e.g., an extruder. The solution can be shaped by passing through an orifice plate or extrusion die, and upon cooling, the thermoplastic material crystallizes and phase separates from the second material. The crystallized thermoplastic material is often stretched. The second material is optionally removed either before or after stretching, leaving a porous polymeric structure. Microporous TIPS membranes are further disclosed in U.S. Pat. No. 4,529,256 (Shipman); U.S. Pat. No. 4,726,989 (Mrozinski); U.S. Pat. No. 4,867,881 (Kinzer); U.S. Pat. No. 5,120,594 (Mrozinski); U.S. Pat. No. 5,260,360 (Mrozinski); and U.S. Pat. No. 5,962,544 (Waller, Jr.). Some exemplary TIPS membranes comprise poly(vinylidene fluoride) (PVDF), polyolefins such as poly(ethylene) or poly(propylene), vinyl-containing polymers or copolymers such as ethylene-vinyl alcohol copolymers and butadiene-containing polymers or copolymers, and acrylate-containing polymers or copolymers. TIPS membranes comprising PVDF are further described in U.S. Pat. No. 7,338,692 (Smith et al.).

The microporous membrane of the present disclosure is treated to comprise a guanidyl functional group. Such functional groups comprise guanidine groups of Formula II or biguanidine groups of Formula III:

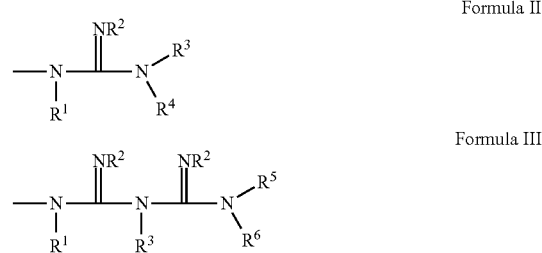

Formula II

Formula III wherein $R^1$, $R^2$, $R^3$, $R^4$, $R^5$, and $R^6$ are independently selected from H or hydrocarbyl, preferably $C_1$-$C_2$ alkyl.

The guanidyl functional group is covalently bonded to the porous membrane substrate using techniques known in the art. Typically, the guanidyl functional group is grafted via a linking group directly onto the porous membrane substrate or onto a membrane substrate that has been treated with a primer layer.

In one embodiment, a porous membrane is treated with guanidyl groups derived from ligand-functional monomer units of the Formula IVa or b:

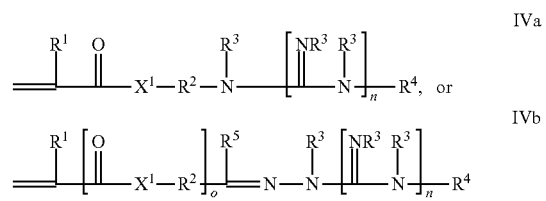

IVa

IVb wherein $R^1$ is H or $C_1$-$C_4$ alkyl; $R^2$ is a (hetero)hydrocarbyl group, optionally containing an ester, amide, urethane or urea, preferably a divalent alkylene having 1 to 20 carbon atoms; each $R^3$ is independently H or hydrocarbyl, preferably $C_1$-$C_{12}$ alkyl; $R^4$ is H, $C_1$-$C_{12}$ alkyl or —$N(R^3)_2$; $R^5$ is H or hydrocarbyl, preferably $C_1$-$C_{12}$ alkyl or aryl; $X^1$ is —O— or —$NR^-$, o is 0 or 1, and n is 1 or 2.

Such guanidyl-containing monomers may be made by condensation of an alkenyl or alkenoyl compound, typically a (meth)acryloyl halide, a (meth)acryloylisocyanate, or an alkenylazlactone, with a compound of Formulas Va or Vb:

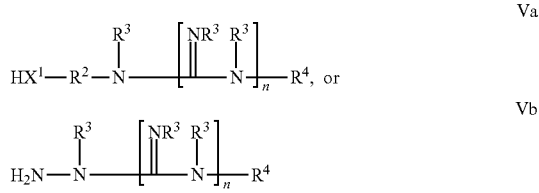

where $R^1$ is H or $C_1$-$C_4$ alkyl; $R^2$ is a (hetero)hydrocarbyl group, optionally containing an ester, amide, urethane or urea, preferably a divalent alkylene having 1 to 20 carbon atoms; each $R^3$ is independently H or hydrocarbyl, preferably $C_1$-$C_{12}$ alkyl; $R^4$ is H, $C_1$-$C_{12}$ alkyl or —$N(R^3)_2$; and $X^1$ is —O— or —$NR^3$—. Other ligand monomers may be made by condensation of a carbonyl containing monomer, such as acrolein, vinylmethylketone, diacetone acrylamide or acetoacetoxyethylmethacrylate, optionally in the presence of a reducing agent, with a compound of Formulas Va or Vb.

U.S. Pat. Publ. No. 2012/0252091 (Rasmussen et al.) discloses treating a porous substrate with a crosslinked polyamine polymer layer having ethyleneically unsaturated polymerizable groups, then grafting to this primer layer a polymer derived from the guanidyl-containing monomers above. U.S. Pat. Publ. No. 2015/0136698 (Bothof et al.) teaches grafting a substrate with the guanidyl-containing monomers above in the presence of a Type II photoinitiator. A Type II photoinitiator is an initiator which, when activated by actinic radiation, forms free radicals by hydrogen abstraction from a second (H-donor) compound to generate the actual initiating free radical. Such photoinitiators are known in the art.

In one embodiment, the grafted polymer layer derived from the guanidyl-containing monomer is a homopolymer of guanidyl monomer units.

In one embodiment, the grafted polymer layer derived from the guanidyl-containing monomer is a copolymer of guanidyl monomer units.

In addition to the guanidyl-containing monomer, in one embodiment, the grafted polymer layer derived from the guanidyl-containing monomer may be derived from other monomers such as multifunctional (meth)acryloyl monomers, including (meth)acrylate and (meth)acrylamide monomers. Examples of useful multifunctional (meth)acrylates include, but are not limited to, di(meth)acrylates, tri(meth) acrylates, and tetra(meth)acrylates, such as ethyleneglycol di(meth)acrylate, 1,6-hexanediol di(meth)acrylate, poly(ethylene glycol) di(meth)acrylates, polybutadiene di(meth) acrylate, polyurethane di(meth)acrylates, and propoxylated glycerin tri(meth)acrylate, methylenebisacrylamide, ethylenebisacrylamide, hexamethylenebisacrylamide, diacryloylpiperazine, and mixtures thereof. In one embodiment, the polymer layer may be derived from hydrophilic monomers, which comprise at least one alkenyl group, preferably a (meth)acryloyl group, and a hydrophilic group, including poly(oxyalkylene) and ionic groups, for providing hydrophilicity to the substrate, or for providing greater selectivity to the substrate when binding biomaterials. The hydrophilic ionic groups may be neutral and/or have a positive charge. In one embodiment, a negatively charge comonomer may be included as long as it is in small enough amounts that it doesn't interfere with the binding interaction of the guanidyl groups.

In one embodiment, the second filtration medium comprises at least 0.01, 0.05, 0.1, or even 0.5 mmol; and at most 1, 1.5, or even 2 mmol of guanidyl groups per gram of the functionalized microporous membrane.

In one embodiment, the thickness of the second filtration medium is at least 5, 10, 20, 25, or even 50 micrometers thick; and at most 800, 500, 200, or even 100 micrometers thick.

As disclosed herein, the combination of the first and second filtration mediums are used as the filtration media. When used in a filtration application, in one embodiment, one or more layers of the first filtration medium may be used. When a plurality of first filtration medium layers is used, each layer may have the same, or different effective fiber diameter, basis weight, solidity, amount of quaternary ammonium grafted, tensile strength, and surface area. In some embodiments, each subsequent layer of the first filtration medium may have a smaller effective fiber diameter so that finer contaminants may be retained. When a plurality of the second filtration medium is used, each layer may have a symmetric or asymmetric (e.g., gradient) distribution of pore size through the direction of fluid flow, and the layers may have the same, or different mean flow pore size, porosity, amount of grafted guanidyl groups, tensile strength, and surface area. In some embodiments, each subsequent layer of the second filtration medium may have a smaller effective pore size so that finer contaminants may be filtered.

The number of layers of the first filtration medium may vary (or be optimized) based on the sample matrix, and/or the type and/or amount of contaminants in the biological fluid. For example, the number of layers of the first filtration medium may vary to optimize the concentration of quaternary ammonium ions present based on the amount of cell debris and/or DNA in the sample. The number of layers of the second filtration medium may vary to optimize the concentration of guanidyl groups present based on the amount of host cell protein in the sample.

In the present disclosure, the first filtration medium is placed upstream of the second filtration membrane. In one embodiment, the second filtration medium is upstream of a capture chromatography step, wherein the targeted biomolecule is retained on media and then subsequently, and deliberately, released from media to purify and/or concentrate the targeted biomolecule. Such capture steps may involve a chromatography column, such as a protein A column.

In one embodiment, the first filtration medium and the second filtration medium are contained in separate housings wherein the first filtration medium is upstream of the second filtration medium. More preferably, the first filtration medium and the second filtration medium are contained in the same housing.

In some embodiments a microporous, non-functionalized size exclusion membrane is disposed between the first filtration medium and the second filtration medium. A microporous membrane is defined above. The membrane is non-functionalized meaning, that the membrane is substantially devoid (i.e., less than 10, 1, or even 0.1 μmol per gram of non-functionalized size exclusion membrane) of ion exchange functional chemical groups. The membrane is a size exclusion membrane, meaning that it retains particles primarily by mechanical sieving. When included, the non-functionalized size exclusion membrane advantageously has a bubble point pore size, as measured according to ASTM Standard Test Method No. F316-03, "Standard Test Methods for Pore Size Characteristics of Membrane Filters by Bubble Point and Mean Flow Pore Test," smaller than that of the second filtration medium.

In one embodiment, the non-functionalized size exclusion membrane comprises an asymmetric pore structure. In one embodiment, the non-functionalized size exclusion membrane comprises a gradient or multizone pore morphology, with the pore size decreasing from the upstream surface toward the downstream surface, to provide a high particle loading capacity. Suitable microporous, non-functionalized size exclusion membrane types include those described above as suitable substrates for the second filtration medium.

In some embodiments, the present disclosure provides a filter device comprising a housing which has a top wall, a bottom wall, a generally cylindrical side wall extending between the top wall and the bottom wall, a filter element disposed within the housing comprising an inlet and an outlet defining a liquid flow path through the filter element. The liquid flow path has an upstream portion adjacent the inlet and a downstream portion adjacent the outlet so that the fluid flows through the first filtration medium and then through the second filtration medium to the outlet.

In one embodiment, the first and second filtration mediums may be each individually configured as a planar or lenticular disk. In some embodiments, the first and second filtration mediums may be each individually pleated.

Preferably, the first and second filtration mediums are located in close proximity, more preferably the first filtration medium and the second filtration medium are housed within the same filter housing. In one embodiment, the first and second filtration mediums are configured as a planar or lenticular disk. In some embodiments, the first and second filtration mediums are pleated together. In one embodiment, the second filtration medium is wrapped around a core and the first filtration medium is wrapped about the second filtration medium. Alternatively, the second filtration medium is disposed onto the first filtration medium to form a multilayered construction, wherein a single layer of the multilayered construction is wrapped around the circumference of a core and bonded together parallel to the core axis, wherein the second filtration medium is downstream from the first filtration medium. Exemplary embodiments are shown in the following figures.

FIG. 1 depicts an exemplary filter media 10 according to the present disclosure comprising first filtration medium 1 (nonwoven with quaternary ammonium groups) and second filtration medium 2 (porous membrane with guanidyl groups). An optional, non-functional layer (not shown) such as a particle size filter, may be disposed between the first filtration medium and the second filtration medium. As shown, filter media 10 comprises a plurality of pleats 4. In some embodiments, pleated filter media 10 may be incorporated into a filter device. Examples of pleating configurations and filter devices comprising pleated media may be found, for example, in U.S. Pat. No. 6,521,011 (Sundet et al).

Figure 2:
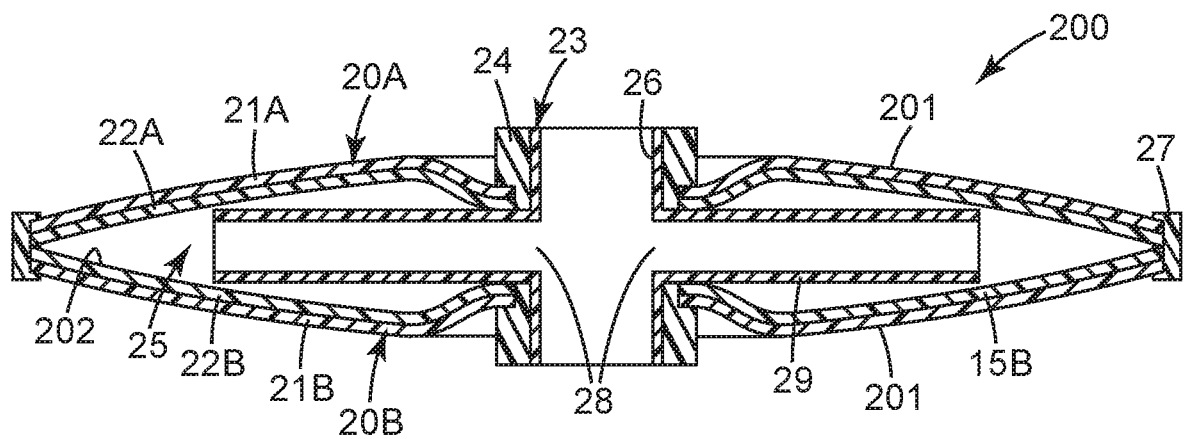
FIG. 2 is a cross-sectional view of an exemplary filter device provided in lenticular form and comprising a filtration medium sequence according to the present disclosure.

FIG. 2 depicts an internal cross-sectional view of an exemplary filter device 200 according to the present disclosure comprising the filter medium sequence in the form of a lenticular filter cell. The lenticular filter cell comprises two disc-like sections of filtration media, identified as filter medium sequence 20A and filter medium sequence 20B, between which is an inner volume 25. The filter medium sequence extends from outer seal 27 to inner seal 24 at central core 26. Together, filter medium sequence 20A and filter medium sequence 20B are referred to as a media pack. In some embodiments, the media pack may be a pocket-like extension of filter media, for example, folded upon itself, not needing an outer seal. When the fluid flow is from the exterior of filter device 200 to interior 25, the outer surface of filter medium sequence 20A, and 20B (designated as 201 in FIG. 2) is the dirty-side or upstream side of filtration medium sequence 20A and 20B and the inner surface of filter medium sequence 20A and 20B (designated as 202 in FIG. 2) is the filtered-side or downstream side of the filter medium sequence. Under such fluid flow conditions, filter medium sequence 20A comprises first filtration medium 21A and second filtration medium 22A while filter medium sequence 20B comprises first filtration medium 21B and second filtration medium 22B. An optional, non-functional layer (not shown) such as a particle size filter, may be disposed between the first filtration medium and the second filtration medium.

Central core 26 has a plurality of radial passages 28 therein which provide fluid communication, in a radial manner, between interior 25 and hub arrangement 23. A separator element 29, which, for example, is composed of a plurality of ribs, extends from hub arrangement 23 into interior 25 between filter medium sequences 20A and 20B. Separator element 29 is a non-filtering element that facilitates fluid flow from interior 25 via radial passages 28 to hub arrangement 23. Additionally, separator element 29 inhibits collapse of filter medium sequence 20A and 20B into interior 25, for example, due to pressure of filter medium sequence 20A and 20B from fluid being filtered by lenticular filter cell 200. As depicted in FIG. 2, separator element 29 has an outer diameter smaller than the outer diameter of filter medium sequences 20A and 20B. In some embodiments, the separator element 29 may have an outer diameter equal to, or slightly greater than, the outer diameter of filter medium sequences 20A and 20B, such that the separator element 29 is encapsulated within outer seal 27.

Although FIG. 2 is described in an operation wherein the fluid flow is from the outside of the lenticular cell into the interior, the lenticular cell may also be run in the reverse direction, wherein the fluid flow is from the inside and proceeds outward. When the fluid flow is in the above-described direction, surface 202 would be the dirty-side or upstream side of filter medium sequence and surface 201 would be the filtered-side or downstream side of filter sequence. Under these fluid flow conditions, the first filtration medium would be located in the interior of the lenticular cell and the second filtration medium would be located downstream of the first filtration medium.

Examples of lenticular filter cells and methods of making lenticular filter cells may be found, for example, in U.S. Pat. No. 6,464,084 (Pulek); U.S. Pat. No. 6,939,466 (Pulek); U.S. Pat. No. 7,178,676 (Pulek et al.); and U.S. Pat. No. 6,712,966 (Pulek et al); and in U.S. Pat. Publ. No. 2011/0259812 (Marks et al). Lenticular filter cells may be used, for example, in conjunction with filtration systems disclosed in U.S. Pat. Publ. No. 2011/0297604 (Bryan et al).

Figure 3:
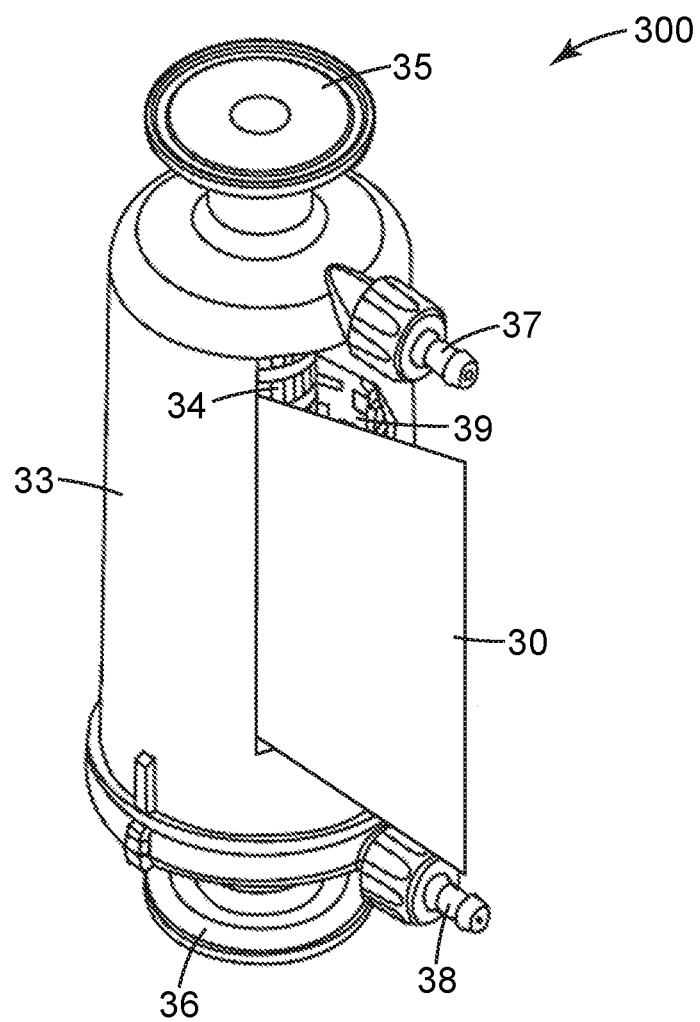
FIG. 3 is a perspective and partial cutaway view of an exemplary filter device provided in encapsulated form and comprising a filtration medium sequence according to the present disclosure.

FIG. 3 is an exemplary filter device 300 comprising filter capsule 33. Filter medium sequence 30 is encapsulated in filter capsule 33, which comprises fluid inlet 35 and fluid outlet 36. Vent valve 37 is used to expel air from the filter device while drain valve 38 is used to drain the filter device after use. As seen in the cut through of FIG. 3, the filter device comprises perforated inner core 34 that extends coaxially through filter capsule 33 fluidly connecting filter medium sequence 30 to fluid outlet 36. Filter medium sequence 30 is shown extending from filter capsule 33 to show the elements of the filter device, however in use, the filter medium sequence is located between perforated inner core 34 and perforated outer periphery 39, which can be seen in FIGS. 3 and 4. Fluid inlet 35 is fluidly connected to perforated outer periphery 39. In operation, fluid enters fluid inlet 35, then sequentially travel through perforated outer periphery 39, filter medium sequence 30, perforated inner core 34, and then exits out fluid outlet 36. Perforated outer periphery 39 may be a netting, perforated cage, etc. used to support the filter medium sequence, especially in backflushing operations. Depending on the construction of the filter medium sequence, the filter device may not comprise a perforated outer periphery.

Figure 4:
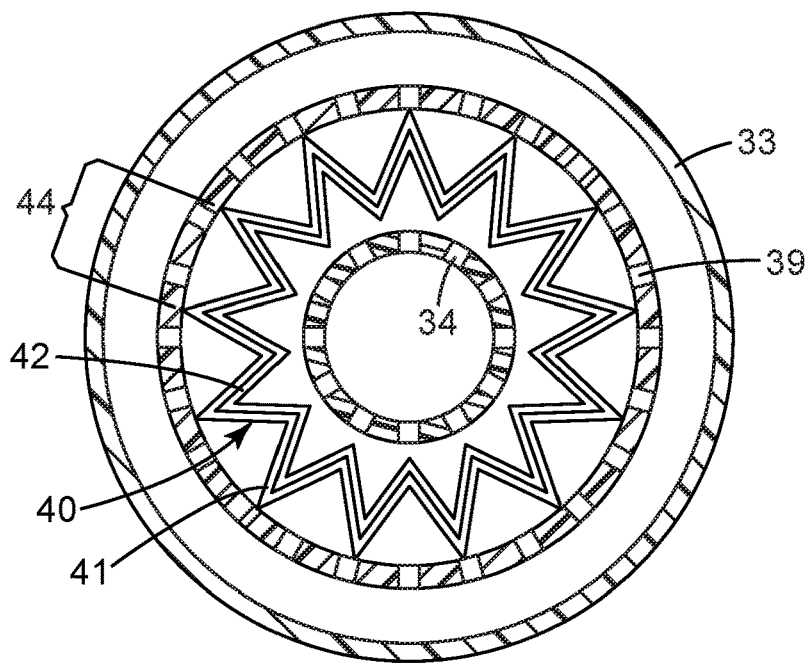
FIG. 4 is a cross-sectional view taken at 4-4 of FIG. 3 of an exemplary filter device provided in encapsulated form and comprising a pleated media cylinder comprising the filtration medium sequence according to the present disclosure.
Figure 5:
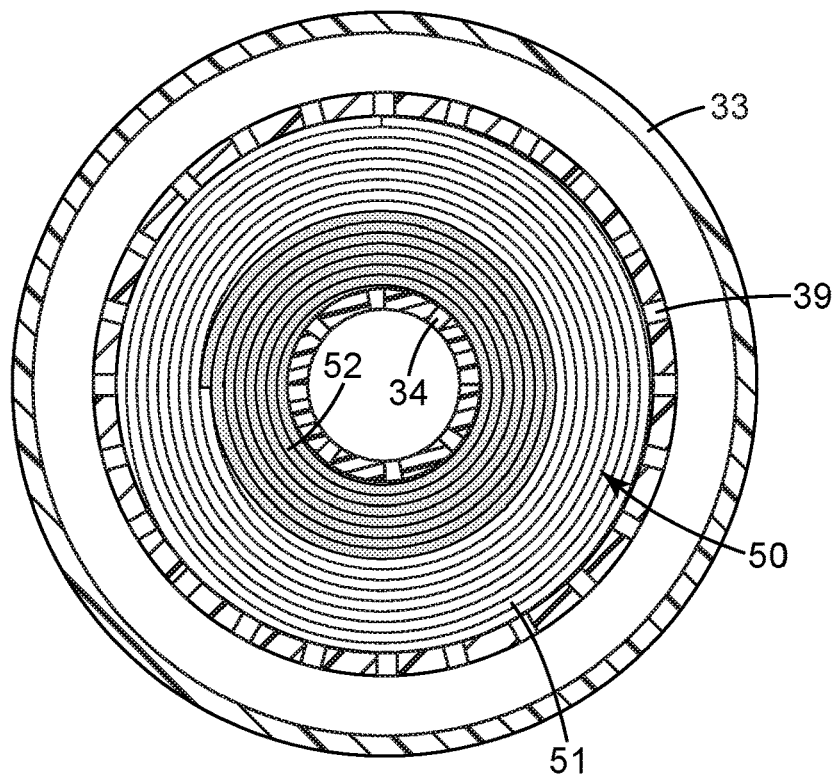
FIG. 5 is a cross-sectional view taken at 4-4 of FIG. 3 of an exemplary filter device provided in encapsulated form and comprising a core wherein the filtration medium sequence according to the present disclosure is spirally wound about the core.

Two different media cylinders for use in filter capsule 33 are shown in FIGS. 4 and 5.

FIG. 4 depicts a cross-sectional view of one embodiment of a filter device, wherein the media capsule comprises a filter medium sequence comprising a plurality of pleats 44. Filter medium sequence 40 located between perforated outer periphery 39 and perforated inner core 34, comprises first filtration medium 41 and second filtration medium 42. Second filtration medium 42 is positioned downstream of first filtration medium 41, where fluid flow is from perforated outer periphery 39, travels through filter medium sequence 40 into perforated inner core 34. An example of a filter module comprising a media cylinder comprising a plurality of pleats may be found, for example, in U.S. Pat. No. 6,315,130 (Olsen).

FIG. 5 depicts a cross-sectional view of an alternative embodiment of a filter device, wherein the media capsule comprises a filter medium sequence spirally wound around inner perforated core 34. Filter medium sequence 50 located between perforated outer periphery 39 and perforated inner core 34, comprises second filtration medium 52 spirally wound about inner perforated core 34 and first filtration medium 51 spirally wound about second filtration medium 52. As drawn, fluid flows from perforated outer periphery 39, through filter medium sequence 50, then into perforated inner core 34. In some embodiments, a drainage layer may be further provided to help facilitate fluid flow between adjacent layers of the filter medium sequence.

In one embodiment, the first and second filtration mediums are encapsulated with a porous web to provide support and aid in handling. In filtration applications, the first and second filtration mediums may be disposed either vertically, or horizontally.

The filtration media sequence of the present disclosure may be used in the purification and/or isolation of targeted biomaterials from a biological fluid. In one embodiment, the filtration media sequence of the present disclosure may be used in the purification and/or isolation of positively charged proteins, more preferably monoclonal antibodies from a harvest fluid from a bioreactor or fermenter. Typically, the harvest fluid comprises, in addition to the monoclonal antibodies, whole cells and insoluble cell debris, and soluble impurities, including protein impurities, such as host cell proteins, DNA, and chromatin in a culture medium.

Monoclonal antibodies are one of the most used therapeutic proteins in the pharmaceutical industry. Advances in cell line development and optimization of cell culture processes have enabled higher antibody titers, which increases cell culture density and lengthens culture duration. This translates into higher levels of process-related impurities such as host cell proteins and DNA, lipids, colloids and cell debris. These higher impurity levels present challenges to the recovery, purification, and/or concentration of the monoclonal antibody. Typically, the post-harvest processing involves primary recovery of the monoclonal antibody, followed by capture of the monoclonal antibody on a chromatography column (such as protein A or cation-exchange chromatography), followed by elution (and concentration) of the captured monoclonal antibody from the chromatography column, and polishing of the eluate.

Protein A affinity chromatography is preferred for capture because of protein A's highly specific interaction with monoclonal antibodies. As protein A columns are relatively expensive, it is important to reduce the impurities in the harvested broth prior to exposure to the protein A column to maximize its life. Furthermore, some impurities may be retained by the protein A column and eluted with the monoclonal antibody eluate, resulting in additional, and/or more aggressive polishing of the eluate.

Cell debris generally refers to insoluble components of lysed (broken) cells, including the cell wall lipids, organelles (e.g., mitochondria, lysosomes, vesicles, and the like), and proteinaceous aggregates. Typically, cell debris are larger, predominantly negatively-charged material that can clog filters. Turbidity is one way to measure the concentration of cell debris in a fluid, where the higher the turbidity value the more cell debris present. In one embodiment, the harvest fluid or cell culture fluid has turbidity of at least 40, 60, 80 or even 100 NTU (nephelometric turbidity unit) and at most 500, 400, 200, or even 150 NTU. After passing through the filter media of the present disclosure, the turbidity of the filtrate is often less than 15, 10, 5, or even 2 NTU.

Undesired proteins, such as protein impurities and host cell proteins, are also typically present in the harvest fluid. In one embodiment, the harvest fluid or cell culture fluid has a host cell protein concentration of at least 50,000; 100,000 or even 200,000 ng/mL and at most 2,000,000; 1,000,000; or even 500,000 ng/mL. These soluble proteins are smaller in nature and need to be separated from the monoclonal antibodies.

DNA, is a nucleotide sequence, which is the blueprint for replication of the cell. In one embodiment, the harvest fluid or cell culture fluid has a concentration of DNA of at least $10^5$, $10^6$, $10^7$, $10^8$, or even $10^9$ picograms/mL. After passing through the filtration media sequence of the present disclosure, the DNA of the filtrate can be reduced by a log reduction value of 3 or greater, many times by a log reduction of 4 or greater, even a log reduction value of 8 or greater.

To isolate and/or purify the targeted biomacromolecule, such as the monoclonal antibody, each of the contaminants must be removed to sufficient levels. Often the culture media comprises buffers, electrolytes, and/or sugars, which can impact the performance of the filter. In one embodiment, the harvest fluid or cell culture fluid has a conductivity of at least 10 milliSiemens/cm (mS/cm), or even 15 mS/cm, and at most not more than 25 mS/cm or even 35 mS/cm. In some embodiments, wherein the filtration medium sequence is used in the process of purification and/or isolation, the inlet fluid (i.e., fluid to be filtered) may have a higher or lower conductivity depending on the previous processing steps. In one embodiment, the inlet fluid has a conductivity of at least 1 mS/cm, or even 0.5 mS/cm, and at least not more than 40 mS/cm or even 50 mS/cm. Sometimes, during traditional isolation/purification of monoclonal antibodies, the process solution is diluted to decrease the ionic concentration, because the high salt concentrations can interfere with certain techniques, such as ion exchange.

It has been discovered in the present application that when a nonwoven substrate functionalized with a quaternary ammonium groups is placed upstream from a microporous membrane functionalized with ligands having guanidine or biguanide groups, a filtration device can be fashioned that has a high capacity for purification of cell debris from the fluid, a high capacity for substantial reduction of DNA from the fluid, and a high degree of host cell protein reduction, while also minimizing the number of process steps.

When utilized in the purification of monoclonal antibodies, the first filtration medium can serve to remove whole cells and cell debris, and soluble contaminants such as DNA and some host cell protein. The second filtration medium comprises guanidyl groups can bind the negatively-charged contaminants, particularly negatively charged host cell proteins, allowing positively charged materials, such as monoclonal antibodies (mAb), to pass through.

In one embodiment, the filtration sequence of the present disclosure can be used to effectively remove cell debris, DNA, and host cell protein, in the presence of high salt concentrations, enabling the purification and/or isolation of targeted biomacromolecules such as mAb.

As will be illustrated in the Examples below, it has been discovered that employing a multilayer construction comprising the first filtration medium upstream from the second filtration medium, yields surprisingly better throughput compared to the filters comprising only quaternary ammonium groups or guanidyl groups. It has also been discovered that the combination of these two filtration mediums, wherein the first filtration medium is upstream from the second filtration medium provides improved throughput, and can extend the life of the filter media combination. The improved throughput can come not only from the improved throughput through the filtration media, but also in removing one or more process step in the purification or isolation of a biological material, and/or more effectively reduce the contaminants to minimize exposure of contaminants to downstream processes, thereby increasing the downstream component's lifetime. When deployed early in the protein purification process, e.g., during initial clarification of the harvested cell culture fluid, or a centrifuged centrate thereof, filtration media of the instant disclosure can also serve to limit the exposure time of the target protein (e.g., mAb) to fluid contaminants (e.g., protease enzymes) that can degrade the quality of the target protein.

EXEMPLARY EMBODIMENTS OF THE PRESENT DISCLOSURE INCLUDE THE FOLLOWING NON-LIMITING EMBODIMENTS

Embodiment 1

A filtration medium sequence comprising:
(i) a first filtration medium comprising an anion exchange nonwoven substrate, wherein the anion exchange nonwoven substrate comprises a plurality of quaternary ammonium groups; and
(ii) a second filtration medium comprising a functionalized microporous membrane wherein the functionalized microporous membrane comprises a plurality of guanidyl groups;
wherein the first filtration medium is positioned upstream of the second filtration medium.

Embodiment 2

The filtration medium sequence of embodiment 1, wherein the first filtration medium comprises at least 0.1 mmol of quaternary ammonium groups per gram of the first filtration medium.

Embodiment 3

The filtration medium sequence of any one of the previous embodiments, wherein the second filtration medium comprises at least 0.01 mmol of guanidyl groups per gram of the second filtration medium.

Embodiment 4

The filtration medium sequence of any one of the previous embodiments, wherein the anion exchange nonwoven substrate has an effective fiber diameter of 1 to 6 micrometer.

Embodiment 5

The filtration medium sequence of any one of the previous embodiments, wherein the second filtration medium has a mean flow pore size of 0.1 to 5 micrometers.

Embodiment 6

The filtration medium sequence of any one of the previous embodiments, wherein the first filtration medium comprises a polymer grafted to the surface of a nonwoven substrate wherein the polymer comprises interpolymerized monomeric units of:
(a) 80 to 98 wt. % of an aminoalkyl (meth)acryloyl monomer;
(b) 2 to 20 wt. % of a poly(alkylene oxide) monomer; and
(c) 0 to 10 wt. % of a second hydrophilic monomer.

Embodiment 7

The filtration medium sequence of any one of embodiments 1-6, wherein the second filtration medium comprises a polymer grafted to the surface of a nonwoven substrate wherein the polymer comprises interpolymerized monomeric units of:
(a) 10 to 50 wt. % of a quaternary ammonium-containing ligand monomer;
(b) 10 to 80 wt. % of an amide monomer;
(c) 10 to 40 wt. % of an oxy monomer; and
(d) 0 to 30 wt. % of a poly(alkylene oxide) monomer.

Embodiment 8

The filtration medium sequence of any one of the previous embodiments, wherein the functionalized microporous membrane comprises a TIPS membrane.

Embodiment 9

The filtration medium sequence of any one of embodiments 1-8, wherein the functionalized microporous membrane comprises a SIPS membrane.

Embodiment 10

The filtration medium sequence of any one of the previous embodiments, wherein the functionalized microporous membrane comprises a free-radically grafted guanidyl-functional (meth)acryloyl monomer, wherein the guanidyl-functional (meth)acryloyl monomer comprises at least one of:

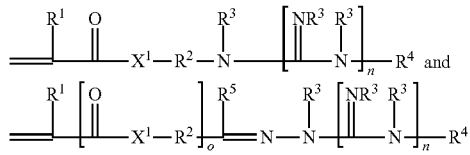

wherein
$R^1$ is H or $C_1$-$C_4$ alkyl;
$R^2$ is a (hetero)hydrocarbyl group;
each $R^3$ is independently H or hydrocarbyl;
$R^4$ is H, $C_1$-$C_{12}$ alkyl or —$N(R^3)_2$;
$R^5$ is H or hydrocarbyl;
$X^1$ is —O— or —$NR^3$—;
o is 0 or 1, and
n is 1 or 2.

Embodiment 11

The filtration medium sequence of embodiment 10, wherein the free-radically grafted guanidyl-functional (meth)acryloyl monomer is grafted to a primer layer disposed on a microporous membrane, wherein the primer layer comprises a cross-linked polyamine polymer having ethylenically unsaturated polymerizable groups, wherein the cross-linked polyamine polymer having ethylenically unsaturated polymerizable groups is a reaction product of: (a) a polyamine polymer; (b) a polyfunctional crosslinking agent for the polyamine polymer; and (c) a monomer having an amine-reactive functional group and an ethylenically unsaturated polymerizable group.

Embodiment 12

The filtration medium sequence of any one of embodiments 10-11, wherein the free-radically grafted guanidyl-functional (meth)acryloyl monomer is grafted on a microporous membrane in the presence of a Type II photoinitiator.

Embodiment 13

The filtration medium sequence of any one of the previous embodiments, wherein the first filtration medium contacts the second filtration medium.

Embodiment 14

The filtration medium sequence of any one of the previous embodiments, comprising a multilayer article, wherein the multilayer article comprises the first filtration medium and the second filtration medium.

Embodiment 15

The filtration medium sequence of any one of the previous embodiments, further comprising a non-functionalized filtration medium disposed between the first filtration medium and the second filtration medium.

Embodiment 16

The filtration medium sequence of embodiment 15, wherein the non-functionalized filtration medium is a microporous, non-functionalized size exclusion membrane.

Embodiment 17

The filtration medium sequence of embodiment 16, wherein the microporous, non-functionalized size exclusion membrane has an asymmetric pore structure.

Embodiment 18

The filtration medium sequence of embodiment 16, wherein the microporous, non-functionalized size exclusion membrane has a mean flow pore size less than the second filtration medium.

Embodiment 19

A filter device comprising
a fluid inlet;
a fluid outlet; and
a filtration media fluidly connecting the fluid inlet and the fluid outlet, wherein the filtration media comprises (i) a first filtration medium comprising an anion exchange nonwoven substrate, wherein the anion exchange nonwoven substrate comprises a plurality of quaternary ammonium groups; and (ii) a second filtration medium comprising a functionalized microporous membrane wherein the functionalized microporous membrane comprises a plurality of guanidyl groups; and wherein the first filtration medium is positioned upstream of the second filtration medium, the filtration media.

Embodiment 20

The filter device of embodiment 19, wherein the filtration media is formed into a media cylinder comprising a plurality of pleats.

Embodiment 21

The filter device of embodiment 19 further comprising a core, wherein the second filtration medium is wound around the core and the first filtration medium is wound around the second filtration medium.

Embodiment 22

The filter device of embodiment 19, wherein the filter device further comprising
a separator element;
an edge seal;
wherein the separator element comprises
a central core in fluid communication with the fluid inlet;
a first side; and
a second side; and
wherein the filter media further comprises
a first media disk positioned on the first side of the separator element and having an outer circumferential edge and an inner circumferential edge; and a second media disk positioned on the second side of the separator element and having an outer circumferential edge and an inner circumferential edge; and wherein the outer circumferential edges of the first and second media disks are connected by the edge seal and the inner circumferential edges of the first and second media disks are connected to the central core and wherein the upstream side of the first and second media disk comprises the first filtration medium.

Embodiment 23

A method of filtration of a biological fluid, the method comprising:
(a) providing the biological fluid, wherein the biological fluid comprises a targeted biomolecule and contaminants, and
(b) contacting the biological fluid with the filtration medium sequence of any one of the previous embodiments to obtain a filtrate.

Embodiment 24

The method of embodiment 23, wherein the biological fluid has a conductivity of at least 10 mS/cm.

Embodiment 25

The method of any one of embodiments 23-24, wherein the biological fluid has turbidity of at least 40 NTU.

Embodiment 26

The method of any one of embodiments 23-25, wherein the biological fluid has a host cell protein concentration of 100,000 ng/mL to 2,000,000 ng/mL.

Embodiment 27

The method of any one of embodiments 23-26, wherein the biological fluid has a concentration of DNA of at least $10^5$ pg/mL.

Embodiment 28

The method of any one of embodiments 23-27, wherein the filtrate has turbidity of less than 15 NTU.

Embodiment 29

The method of any one of embodiments 23-28, wherein the biological fluid has a first host cell protein concentration and the filtrate has a second host cell protein concentration, wherein the second host cell protein concentration is at least 50% lower than the first host cell protein concentration.

Embodiment 30

The method of any one of embodiments 23-29, wherein the biological fluid has a first DNA concentration and the filtrate has a second DNA concentration wherein the second DNA concentration is at least 3 logs lower than the first DNA concentration.

Embodiment 31

The method of any one of embodiments 23-30, further comprising contacting the filtrate to a chromatography column functionalized with Protein A.

Embodiment 32

The method of any one of embodiments 23-31, wherein the targeted biomolecule is a protein.

Embodiment 33

The method of embodiment 32, wherein the targeted biomolecule is a positively charged protein.

Embodiment 34

The method of embodiment 33, wherein positively charged protein is a monoclonal antibody.

Examples

Unless otherwise noted, all parts, percentages, ratios, etc. in the examples and the rest of the specification are by weight, and all reagents used in the examples were obtained, or are available, from general chemical suppliers such as, for example, Sigma-Aldrich Company, Saint Louis, Mo., or may be synthesized by conventional methods.

These abbreviations are used in the following examples: cm=centimeter; g=grams; mL=milliliter; min=minutes; µL=microliters; mmol=millimol; wt=weight; pg=pictograms; kPa=kilopascal; kV=kilovolt; kGy=kilgray; and ° C.=degrees Celsius.

Materials

Methacrylamidopropyltrimethylammonium chloride (MAPTAC, 50% wt/wt solution in water), methylenebisacrylamide (MBA), benzophenone, and methanol were obtained from Sigma-Aldrich.

4-(3-sulfopropyloxy)benzophenone sodium salt (S-BP) may be prepared as described in Japanese Patent No. 47040913, Teijin Ltd.

N-(3-dimethylaminopropyl)methacrylamide (DMAPMA) and N-vinyl pyrrolidone (NVP) were obtained from TCI Americas, Inc., Portland, Oreg.

Isocyanatoethylmethacrylate agmatine sodium sulfate (IEM-Ag) may be prepared as described in U.S. Pat. Publ. No. 2011-0033633.

Glycidyl methacrylate (GMA) was obtained from Dow Chemical Corporation, Deer Park, Tex.

Nylon membrane substrates (#080ZN, reinforced nylon-6,6 membrane, 0.8 micrometer nominal pore size) were obtained from 3M Purification, Inc., Meriden, Conn.

Polypropylene blown microfiber (PP BMF) substrates were prepared by a meltblown process and had an Effective Fiber Diameter of 4.3 micrometers, basis weight of 90 grams per square meter, and solidity of 10%.

Measurements

Mass Percent of Grafted Polymer and Graft Density Measurement for Functional Nonwovens For functional nonwovens described below, the mass percent of grafted functional polymer was measured as follows. At least five 47-mm diameter discs were die cut from a dried functional nonwoven sample. The discs were dried to a constant weight on a moisture balance (Mettler-Toledo MJ33 available from Metler-Toledo, LLC, Columbus, Ohio) at 90° C., and the constant dry weight was recorded as $m_f$. The mass of an equal area of PP BMF substrate was recorded as $m_a$. The mass percent of grafted polymer was then calculated as, $$\text{Mass \% grafted polymer} = \frac{m_f - m_i}{m_f} \times 100\%.$$

The mass percent of grafted functional polymer was subsequently utilized to estimate the number of millimoles of monomer grafted to the nonwoven substrate by multiplying the mass percent of functional polymer by the total mass of a sample of known area, multiplying the result by the mass percent of ligand functional monomer in the coating solution with respect to total monomer, and dividing by the molecular weight of the ligand functional monomer. Graft density was then normalized by dividing by the original mass of the nonwoven substrate and expressed as millimoles of monomer grafted per gram of substrate (mmol/g).

Graft Density Measurement for Functional Membranes

Nylon membrane substrates were equilibrated for a minimum of 18 hours in a low humidity chamber (Sanpia Dry Keeper, Sanplatec Corporation, available from VWR International) at a relative humidity (RH) of 20-25 percent (%), prior to being grafted. The substrates were removed from the low humidity chamber, weighed immediately, and then subjected to a free radical grafting reaction as described below for a variety of ligand functional group-containing monomers. Following a washing and drying process, the substrates were again equilibrated in the low humidity chamber for a minimum of 18 hours, were removed from the chamber, and were reweighed immediately to obtain a measurement of mass gain during the grafting reaction. The mass gain was subsequently utilized to estimate the number of millimoles of monomer grafted to the membrane substrate by dividing the mass gain by the molecular weight of the monomer. Graft density was then normalized by dividing by the original mass of the membrane substrate and expressed as millimoles of monomer grafted per gram of substrate (mmol/g).

pH and Conductivity

The pH and conductivity values of challenge fluids were characterized using a Beckman Coulter pHI 570 pH and Electrochemistry Meter available from Beckman Coulter, Inc., Brea, Calif.

Turbidity

In filtration experiments, turbidities of the challenge fluids and processed fluids were measured using a turbidimeter (available under the trade designation "ORION AQUA-FAST AQ4500 TURBIDIMETER from Thermofisher Scientific). The turbidimeter provides turbidity values in standard Nephelometric Turbidity Units (NTU).

Quantification of Host Cell Protein (HCP) Concentration by ELISA

Quantification of CHO HCP was performed by using an enzyme-linked immunosorbent assay (ELISA) specific for CHO HCP (CHO HCP ELISA kit, 3G, obtained from Cygnus Technologies, Southport, N.C.). Prior to analysis, samples were diluted with buffer (Sample Dilution Buffer obtained from Cygnus Technologies) to achieve a concentration within the range of the calibration curve.

A % HCP reduction is reported, which is the HCP concentration determined by the difference of the HCP concentration in the challenge fluid (CHO centrate) minus the HCP concentration in the filtrate divided by the HCP concentration in the challenge fluid (CHO centrate) and reported as a percentage.

Sodium Dodecyl Sulfate Polyacrylamide Gel Electrophoresis (SDS-PAGE)

Aliquots for non-native electrophoresis were dissolved in a premixed protein sample buffer (2× Laemmli sample buffer obtained from Biorad Laboratories Inc., Hercules, Calif.) containing β-mercaptoethanol. Samples were run at 200 volts for 30 minutes in a precast 12% Tris-glycine gel (available under the trade designation "CRITERION TGX PRECAST GEL" from Biorad Laboratories Inc.) to separate the various proteins in the aliquot. After electrophoresis was completed, the gel was stained using a silver staining kit from ThermoFisher Scientific.

Quantification of DNA Concentration

Quantification of CHO DNA was performed by quantitative polymerase chain reaction (qPCR) using an assay specifically for CHO DNA (available under the trade designation "RESDNASEQ QUANTITATIVE CHO DNA KIT" from ThermoFisher Scientific, Waltham, Mass.). Prior to qPCR, the DNA was isolated from the samples using a preparation kit (available under the trade designation "PREPSEQ RESIDUAL DNA SAMPLE PREPARATION KIT" from ThermoFisher Scientific) to prevent interference from cell culture media components.

DNA reduction is reported as a LRV (log reduction value), wherein the DNA concentration determined in the filtrate was divided by the DNA concentration in the challenge fluid (CHO centrate) and then the base-10 logarithm of the resulting quotient was taken.

Preparation of Materials

Membrane 1: Quaternary Ammonium Functional Membrane

A quaternary ammonium functional ("Q-functional) Membrane 1 was prepared as follows. Coating Solution: A coating solution was prepared by mixing MAPTAC (3.532 grams of the 50% wt/wt solution in water) and S-BP (250 microliters of a 0.05 g/mL solution in deionized water), then diluting to a total of 20 grams with deionized water.

Preparation: An 18-cm×23-cm nylon membrane substrate was placed on a sheet of polyester film, and the coating solution was pipetted onto the top surface of the substrate. The coating solution was allowed to soak into the substrate for about 1 minute, and then a second sheet of polyester film was placed on top of the substrate. A 2.28 kg cylindrical weight was rolled over the top of the resulting three-layer sandwich to squeeze out excess coating solution. Ultraviolet (UV)-initiated grafting was conducted by irradiating the sandwich using a UV stand (Classic Manufacturing, Inc., Oakdale, Minn.) equipped with 18 bulbs [Sylvania RG2 40W F40/350BL/ECO, 10 above and 8 below the substrate, 1.17 meters (46 inches) long, spaced 5.1 cm (2 inches) on center], with an irradiation time of 15 minutes. The polyester sheets were removed, and the resulting functionalized substrate was placed in a 1000 mL polyethylene bottle. The bottle was filled with 0.9 percent (%) saline, sealed, and shaken for 30 minutes to wash off any residual monomer or ungrafted polymer. The saline was poured off, and the functionalized substrate was washed for another 30 minutes with a fresh saline solution and then washed for 30 minutes with deionized water (2 times) and allowed to dry.

Graft density of the functional Membrane 1 was found to be 0.53 mmol/g.

Membrane 2A: Guanidyl Functional Membrane

A guanidyl functional ("G-functional") Membrane 2 was prepared as follows. Coating Solution: A coating solution was prepared by mixing IEM-Ag (3.5 grams), MBA (0.07 gram), and benzophenone (0.125 gram), then diluting to a total of 25 grams with methanol. The mixture was stirred for 30 minutes, then filtered. A nylon membrane substrate was then coated with the coating solution, irradiated, washed, and dried as described above for the Preparation of Membrane 1. Graft density of the functional Membrane 2A was found to be 0.51 mmol/g.

Membrane 2B: Guanidyl Functional Membrane

A guanidyl functional ("G-functional") Membrane 2B was prepared following the procedure described in U.S. Pat. App. No. 2012/0252091, Example 42.

Membrane 3: Tertiary Amine Functional Membrane

A tertiary amine functional ("T-functional") Membrane 3 was prepared as follows. Coating Solution: A coating solution was prepared by mixing DMAPMA (0.851 gram) and S-BP (250 µL of a 0.05 g/mL solution in deionized water), then diluting to a total of 20 grams with deionized water. A nylon membrane substrate was then coated with the coating solution, irradiated, washed, and dried as described above for the Preparation of Membrane 1. Graft density of the functional Membrane 3 was found to be 0.41 mmol/g.

Nonwoven 1: Quaternary Ammonium Functional Nonwoven

A quaternary ammonium functional ("Q-functional") Nonwoven 1 was prepared following the procedure described in U.S. 2015/0099413. Coating Solution: A coating solution was prepared by mixing aqueous MAPTAC solution (50% wt/wt solution in water), NVP, GMA, and deionized water to make an aqueous solution containing 9 wt % MAPTAC monomer, 11 wt % NVP, 6 wt % GMA, and 74 wt % water. The coating solution was purged of air by repeatedly opening its cover, closing the cover, and shaking the solution under a nitrogen atmosphere inside a glove box.

Preparation: A 30-cm×43-cm sheet of PP BMF substrate was purged of air inside the glove box and inserted into a re-sealable plastic bag which was sealed. The sealed bag was then removed from the glove box and irradiated to a dose level of 40 kGy by passing it through an Energy Sciences, Inc. 'Electrocurtain' CB-300 electron beam in a single-pass operation at a web speed of approximately 5.5 meters/min (18-19 feet/min) and an accelerating voltage of 300 kV. The sealed bag was then returned to the nitrogen atmosphere inside the glove box. The bag was opened and evenly saturated with 110 grams of the nitrogen-purged coating solution and the bag was resealed after expelling most of the nitrogen. During these steps the oxygen level within the glove box was generally maintained below 40 parts per million (ppm). The sample was maintained flat in the bag and saturated with coating solution for about 16 hours. The functionalized nonwoven was then removed, washed, and dried as described in U.S. 2015/0099413. The mass percent of grafted functional polymer was found to be 62 percent (%), corresponding to a MAPTAC graft density of 0.25 mmol/g of functionalized nonwoven or 0.66 mmol/g of nonwoven substrate.

Nonwoven 2: Guanidyl Functional Nonwoven

A guanidyl functional ("G-functional") Nonwoven 2 was prepared as follows. Coating Solution: A coating solution was prepared containing 9 wt % IEM-Ag, 11 wt % NVP, 6 wt % GMA, and 74 wt % deionized water.

Preparation: A PP BMF substrate was then inertly coated, irradiated, washed, and dried as described above for the Preparation of Nonwoven 1. The mass percent of grafted functional polymer was found to be 69 percent (%), corresponding to a IEM-Ag graft density of 0.16 mmol/g of functionalized nonwoven or 0.52 mmol/g of nonwoven substrate.

Nonwoven 3: Tertiary Amine Functional Nonwoven

A tertiary amine ("T-functional") Nonwoven 3 was prepared as follows. Coating Solution: A coating solution was prepared containing 9 wt % DMAPMA, 11 wt % NVP, 6 wt % GMA, and 74 wt % deionized water.

Preparation: A PP BMF substrate was then inertly coated, irradiated, washed, and dried as described above for the Preparation of Nonwoven 1. The mass percent of grafted functional polymer was found to be 61 percent (%), corresponding to a DMAPMA graft density of 0.32 mmol/g of functionalized nonwoven or 0.84 mmol/g of nonwoven substrate.

Challenge Fluids

A culture of Chinese Hamster Ovary cell was done using standard cell culture techniques. The harvest fluid was collected, centrifuged, and then tested for Conductivity or pH, Turbidity, and HCP concentration by ELISA. Various cultures were used in the experiments disclosed herein and the profiles for each are described below.

CHO Centrate 1: A CHO cell culture was harvested at a cell density of approximately $5 \times 10^6$ cells/mL and a viability of roughly 20%. The harvest fluid was centrifuged (Jouan GR4.22 centrifuge available from Thermofisher Scientific) for approximately 4 minutes at 4000 rpm, yielding a centrate fluid with a turbidity of 85.2 NTU, a HCP concentration of 169,596 nanograms per milliliter (ng/mL), and a conductivity of 11.8 mS/cm.

CHO Centrate 2: A CHO cell culture was harvested at a cell density of approximately $1 \times 10^8$ cells/mL, a viability of roughly 60, and a mAb concentration of 0.5 mg/mL. The harvest fluid was centrifuged (Jouan GR4.22 centrifuge available from Thermofisher Scientific) for approximately 8 minutes at 4000 rpm, yielding a centrate fluid with a turbidity of 83.4 NTU, a HCP concentration of 255,688 nanograms per milliliter (ng/mL), a DNA concentration of $2.41 \times 10^8$ pg/mL, and a conductivity of 16.9 mS/cm.

CHO Centrate 3: The cell culture was harvested at a cell concentration of approximately $1 \times 10^7$ cells/mL and a viability of roughly 20%. The fluid was centrifuged, yielding a centrate having a turbidity of 81.0 NTU, a HCP concentration of 259,840 nanograms per milliliter (ng/mL), and a pH of 6.8.

CHO Centrate 4: The cell culture was harvested at a cell concentration of approximately $1 \times 10^7$ cells/mL and a viability of roughly 20%. The fluid was centrifuged, yielding a centrate having a turbidity of 87.5 NTU, a HCP concentration of 265,740 nanograms per milliliter (ng/mL), and a pH of 6.8.

Methods

Filtration Challenge Experiments Using 25-mm Filter Housings

CHO cell challenge fluids were used to perform filtration tests on various nonwoven and membrane media combinations, using nominally 25-mm diameter filter acrylic housings, as follows. 25-mm diameter discs of the functional nonwoven and functional membrane media were die cut from the dried media samples described above. For each tested media combination, six discs of a particular functional membrane media were placed in the bottom of an acrylic filter housing. Four discs of a particular functional nonwoven media were then placed on top of the functional membrane media in the holder. The acrylic housing was then assembled. The acrylic housing was adapted to provide an edge seal about the periphery of the media by means of an o-ring, defining an effective filtration area (EFA) of 2.84 square centimeters ($cm^2$), such that the challenge fluid would flow into an inlet of the housing, then through the four layers of functional nonwoven media, then through the six layers of functional membrane media, then out an outlet of the housing. A vent valve positioned near the fluid inlet enabled venting of the housing of air prior to the test.

Filtration challenges were conducted using a PEN-DOTECH Filter Screening System available from Pen-doTECH, Princeton, N.J. An automated pump module provided a constant flow rate of challenge solution to the filter housing. The pressure drop across the filter housing was monitored using a pressure transducer positioned upstream of the housing inlet. The mass of fluid collected at the outlet of the filter housing was monitored using a mass balance. At any given time, the cumulative quantity of fluid processed through the filter housing was characterized in units of liters of fluid processed per square meter of EFA ($L/m^2$).

Before each filter test, the filter housing was first vented and flushed at a flow rate of 3 mL/min with 250 $L/m^2$ of a 25 millimolar (mM) sodium chloride solution in deionized water. The feed fluid was then changed to the CHO challenge fluid and the filter test was commenced, also at a flow rate of 3 mL/min. During a filter test, the pressure drop increased as the membrane became loaded with particulate matter in the challenge fluid. The filter test was stopped when the pressure reached 172 kPa (25 psi), and the cumulative quantity of fluid processed at that time was recorded as the throughput. Outlet fluid samples for each filter test were collected in individual aliquots of approximately 25 milliters (88 $L/m^2$), the exact mass of each of which was measured and recorded. The turbidity of each aliquot was measured, and selected aliquots were tested for HCP and/or DNA concentration as described above. The mean outlet turbidity for each filter test was calculated as a weighted average of the turbidities of each of the aliquots, weighted by the aliquot masses.

Filtration Challenge Experiments Using 47-mm Filter Housings

CHO cell challenge fluids were used to perform filtration tests on various nonwoven and membrane media combinations, using nominally 47-mm diameter filter housings, as follows. In each challenge experiment, four filter trains were constructed, each with either a single nominally 47-mm diameter acrylic filter housing or two such filter housings arranged in series. 47-mm diameter discs of the media were die cut from the dried media samples described above. Media discs were placed inside the filter housings in particular combinations, as detailed in the examples below. The housings were then assembled. Each acrylic housing was adapted to provide an edge seal about the periphery of the media by means of an o-ring, defining an EFA of 13.85 square centimeters ($cm^2$). A vent valve positioned near the fluid inlet enabled venting of the housing of air prior to the test.

In filter trains where one filter housing was used, the filter housing was arranged such that the challenge fluid passed into a fluid inlet of the housing, then through the filter media inside the housing, then out of a fluid outlet of the housing. In filter trains where two filter housings were used, the filter housings were arranged such that the challenge fluid passed into a fluid inlet of a first housing, then through filter media inside the first housing, then out of a fluid outlet of the first housing, then into a fluid inlet of a second housing, then through filter media inside the second housing, then out of a fluid outlet of the second housing.

Filtration challenges were conducted using a normal flow filtration screening system (3M Purification, Inc., Meriden, Conn.). An automated pump module provided a constant flow rate of challenge solution to each filter train. A pressure transducer was positioned upstream of each filter housing of each filter train, such that the pressure drop across each filter housing could be monitored. In filter trains with two series filter housings, a 3-way valve was installed between the first filter housing and the second filter housing to enable the periodic collection of samples from that position in the filter train by means of a syringe. The mass of fluid collected at the outlet of the last series filter housing of each filter train was monitored using a mass balance. At any given time, the cumulative quantity of fluid processed through the filter housing was characterized in units of liters of fluid processed per square meter of EFA ($L/m^2$).

Before each filter test, the filter housing was first vented and flushed at a flow rate of 4 mL/min with 250 $L/m^2$ of a 35 millimolar (mM) sodium chloride solution in deionized water. The feed fluid was then changed to the CHO challenge fluid and the filter test was commenced at a flow rate of 3.7 mL/min. During a filter test, the total pressure drop across the filter train increased as the membranes became loaded with particulate matter in the challenge fluid. Each filter test was stopped when the total pressure (across all series holders in the filter train) reached 172 kPa (25 psi), and the cumulative quantity of fluid processed at that time was recorded as the throughput.

Examples

Examples 1-2; Comparative Examples C1-C5

Various functional media combinations as described in Table 1 were tested in the Filtration Challenge Experiments Using 25-mm Filter Housings Method using CHO Centrate 1. Throughput, mean outlet turbidity, and HCP reduction results for Examples 1-2 and Comparative Examples C1-C5 are reported in Table 1.

TABLE 1

| Sample | Nonwoven | Membrane | Throughput ($L/m^2$) | Outlet Turbidity | % HCP reduction Aliquot | | | | |
|---|---|---|---|---|---|---|---|---|---|
| | | | | | 1 | 2 | 4 | 5 | 6 |
| 1 | 1 | 2A | 470 | 3.3 | 97 | 86 | 44 | — | 11 |
| C1 | 1 | 1 | 446 | 2.0 | 58 | 24 | 28 | — | 28 |
| C2 | 2 | 2A | 371 | 1.8 | 99 | 95 | — | 80 | — |
| C3 | 2 | 1 | 410 | 1.7 | 96 | 88 | — | 52 | — |
| C4 | 1 | 3 | 462 | 3.1 | 59 | 40 | 36 | — | 34 |
| 2 | 1 | 2A | 340 | 2.6 | — | 91 | 37 | — | — |
| C5 | 3 | 2A | 286 | 4.8 | — | 89 | — | 22 | — |

"—" means not analyzed

Assuming that the upstream membrane impacts the ultimate throughput of the filtration media, the throughput data from Table 1 was consolidated and compared for Nonwoven 1, Nonwoven 2, and Nonwoven 3. The average throughput when Nonwoven 1 was used was 430 $L/m^2$. The average throughput when Nonwoven 2 was used 390 $L/m^2$. The throughput for Nonwoven 3 was 286 $L/m^2$.

Example 3; Comparative Examples C6-C8

Figure 6:
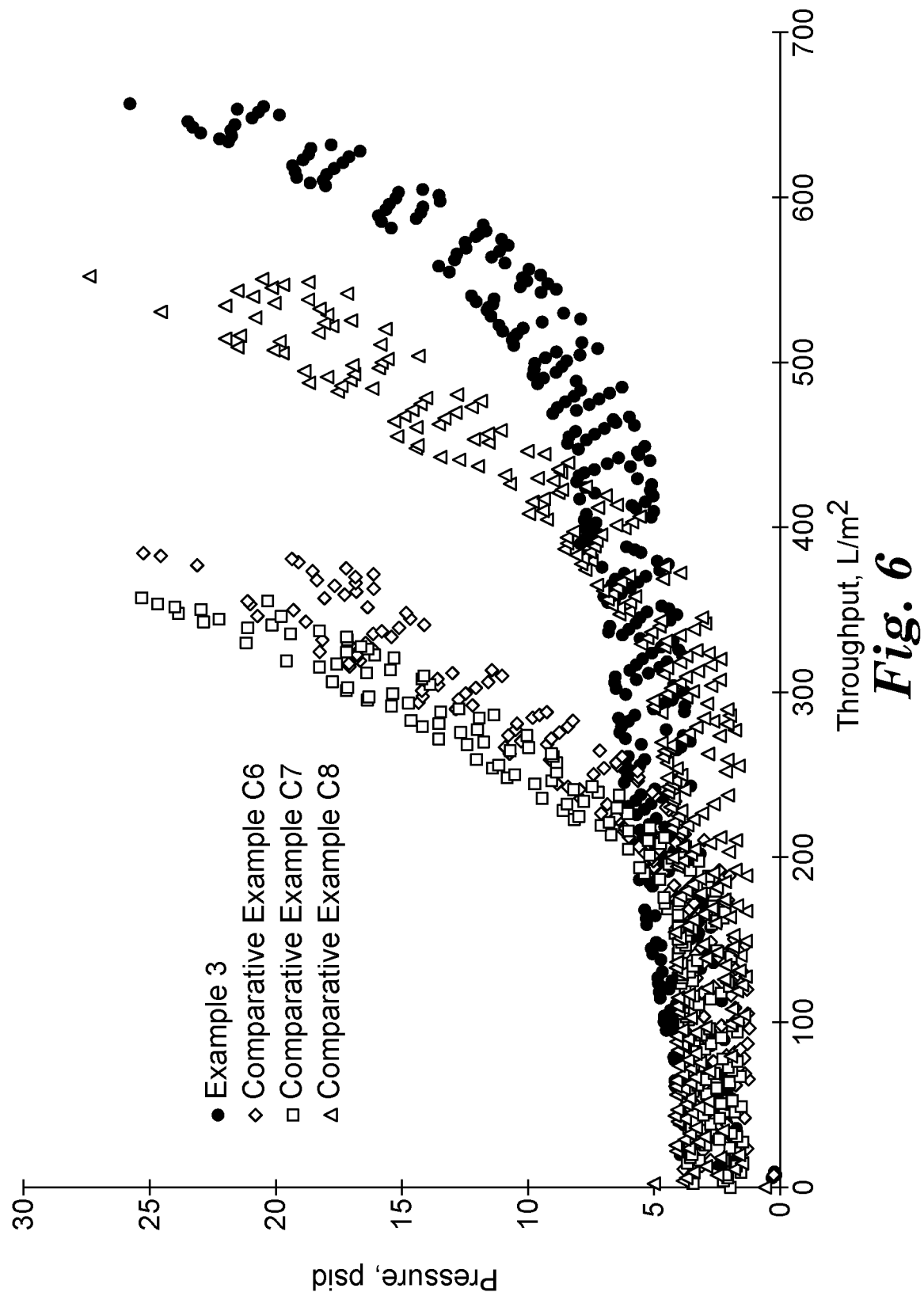
FIG. 6 is a plot of pressure versus throughput for Example 3 and Comparative Examples C6-C8.

The above experiment was redone using a challenge solution with a higher HCP concentration. Various functional media combinations as described in Table 2 were tested in the Filtration Challenge Experiments Using 25-mm Filter Housings Method using CHO Centrate 2. The results of the throughput, mean outlet turbidity, % HCP reduction, and log reduction value (LRV) for DNA reduction for Example 3 and Comparative Examples C6-C8 are reported in Table 2 below. As mentioned above, the pressure drop across the filter housing was monitored during the run as was the mass of the fluid collected, which can be calculated into throughput ($L/m^2$). Shown in FIG. 6 is the pressure as a function of the throughput for Example 3 and Comparative Examples C6-C8.

TABLE 2

| Sample | Nonwoven | Membrane | Throughput ($L/m^2$) | Outlet Turbidity | % HCP reduction Aliquot 1 | % HCP reduction Aliquot 2 | LRV DNA reduction Aliquot 1 | LRV DNA reduction Aliquot 2 |
|---|---|---|---|---|---|---|---|---|
| 3 | 1 | 2A | 657 | 5.7 | 74 | 46 | 6.71 | 7.33 |
| C6 | 2 | 2A | 384 | 3.5 | 82 | 66 | 6.95 | 6.78 |
| C7 | 2 | 1 | 357 | 3.1 | 77 | 46 | 7.53 | 6.32 |
| C8 | 1 | 1 | 552 | 3.4 | 46 | 29 | 7.91 | 7.03 |

Examples 4-5; Comparative Examples C9-C10

Various media were tested in filter trains following the Filtration Challenge Experiments Using 47-mm Filter Housings Method above.

Comparative Example C9 contained only one filter housing, in which were installed two conventional depth filter media grades (available under the trade designations "ZETA PLUS 60ZA" and "ZETA PLUS 90ZA" from 3M Co., St. Paul, Minn. composed of pre-extracted inorganic filter aid, cellulose, and cationic polymer binder). The filter housing contained 1 layer ZETA PLUS 60ZA upstream of 1 layer ZETA PLUS 90ZA.

Comparative Example C10 contained two filter housings arranged in series. The first (upstream) filter housing contained four layers of Nonwoven 1. The second filter housing contained one 0.2-micron rated, asymmetric, non-functionalized nylon size-exclusion membrane which was not functionalized. This filter train simulated a commercially available synthetic clarification filter designed for mammalian cell culture clarification, 3M EMPHAZE AEX Hybrid Purifier, available from 3M Purification, Inc., Meriden, Conn.

Example 4 contained two filter housings arranged in series. The first (upstream) filter housing contained four layers of Nonwoven 1. The second housing contained one 0.2-micron rated, asymmetric, non-functionalized nylon size exclusion membrane upstream of 2 layers of Membrane 2B.

Example 5 was the same configuration as Example 4 except 4 layers of Membrane 2B were used instead of 2.

The four filter trains were simultaneously challenged with CHO Centrate 3 at a flow rate of 3.7 mL/min. Samples were taken from each filter train, at each of two positions, for HCP analysis. The first position (if two housings were used) was downstream of the outlet of housing 1, but upstream of the inlet of housing 2. This enabled calculation of the HCP reduction achieved by the media in housing 1. The second position was downstream of the outlet of housing 2. This enabled calculation of the cumulative HCP reduction achieved by the media in both housings. Samples were taken from each filter train at two throughput points of 145 $L/m^2$ and 220 $L/m^2$, enabling characterization of HCP reduction achieved at an earlier part of the run and a later part of the run, respectively. HCP reductions at each of the positions and throughput points are shown in Table 3. Also shown in Table 3 below is the total throughput and turbidity of the accumulated filtrate for Examples 4-5 and Comparative Examples C9-10.

TABLE 3

| | % HCP Reduction | | | | | |
|---|---|---|---|---|---|---|
| | 145 $L/m^2$ | | 220 $L/m^2$ | | | |
| Sample | After housing 1 | After housing 2 | After housing 1 | After housing 2 | Total Throughput ($L/m^2$) | Turbidity (NTU) |
| C9 | NA | 26 | NA | 0 | 339 | 0.5 |
| C10 | 33 | 26 | 28 | 33 | 422 | 3.0 |
| 4 | 34 | 69 | 31 | 35 | 397 | 4.5 |
| 5 | 26 | 74 | 30 | 68 | 365 | 2.8 |

NA means not applicable

Examples 6-8; Comparative Example C11

Various media were tested in filter trains following the Filtration Challenge Experiments Using 47-mm Filter Housings Method above.

Comparative Example C11 contained only one filter housing, in which were installed four layers of Nonwoven 1 upstream of one 0.2-micron rated, asymmetric, non-functionalized nylon size-exclusion membrane. This filter train simulated a commercially available synthetic clarification filter designed for mammalian cell culture clarification, 3M EMPHAZE AEX Hybrid Purifier, available from 3M Purification, Inc., Meriden, Conn.

Examples 6-8 contained two filter housings arranged in series, the contents of the first (upstream) housing being identical the housing contents of Comparative Example C11. The second housing for Examples 6-8 contained three, four, and six layers, respectively of Membrane 2B.

The four filter trains were simultaneously challenged with CHO Centrate 4 at a flow rate of 3.7 mL/min. When the total pressure drop of each of the filter trains reached 172 kPa (25 psi), the cumulative quantity of fluid processed at that time was recorded as the throughput. The turbidity and HCP concentration of the total pool of accumulated filtrate for each filter train were measured. This enabled calculation of the HCP reduction achieved by each filter train over the entirety of the run. Throughput, total turbidity, and HCP reduction for each of the filter trains are shown in Table 4.

TABLE 4

| Sample | Total Throughput (L/m²) | Turbidity (NTU) | % HCP reduction |
|---|---|---|---|
| C11 | 429 | 0.3 | 36 |
| 6 | 378 | 1.7 | 62 |
| 7 | 419 | 1.3 | 62 |
| 8 | 421 | 2.0 | 72 |

Figure 7:
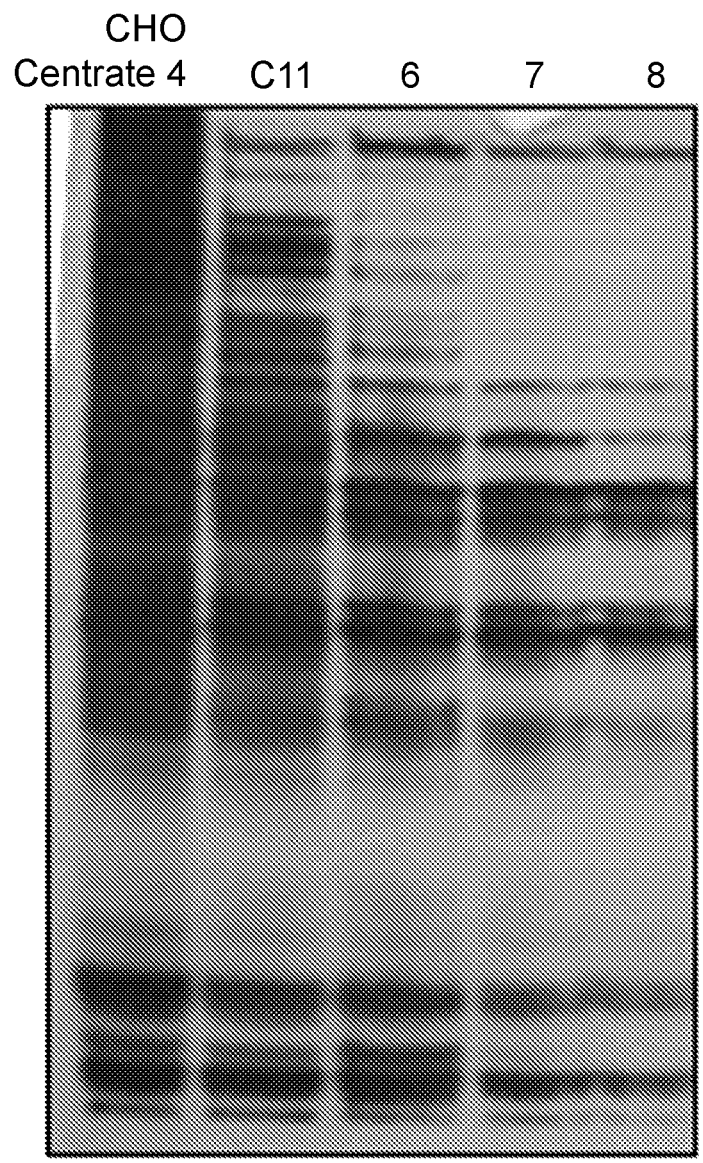
FIG. 7 is a picture of a SDS-PAGE gel of CHO Centrate 4 and the filtrate from Examples 6-8 and Comparative Example C11.

Aliquots from CHO Centrate 4 challenge fluid and each of the filtrate pools from Examples 6-8 and Comparative Example C11 were analyzed by SDS-PAGE. The resulting gel is shown in FIG. 7.

Foreseeable modifications and alterations of this invention will be apparent to those skilled in the art without departing from the scope and spirit of this invention. This invention should not be restricted to the embodiments that are set forth in this application for illustrative purposes. To the extent that there is any conflict or discrepancy between this specification as written and the disclosure in any document mentioned or incorporated by reference herein, this specification as written will control.

What is claimed is:

1. A filtration medium sequence comprising:
   a first filtration medium comprising an anion exchange nonwoven substrate, wherein the anion exchange nonwoven substrate comprises a plurality of quaternary ammonium groups; and
   (ii) a second filtration medium comprising a functionalized microporous membrane wherein the functionalized microporous membrane comprises a plurality of guanidyl groups;
   wherein the first filtration medium is positioned upstream of the second filtration medium.

2. The filtration medium sequence of claim 1, wherein the first filtration medium comprises at least 0.1 mmol of quaternary ammonium groups per gram of the first filtration medium.

3. The filtration medium sequence of claim 1, wherein the second filtration medium comprises at least 0.01 mmol of guanidyl groups per gram of the second filtration medium.

4. The filtration medium sequence of claim 1, wherein the first filtration medium comprises a polymer grafted to the surface of a nonwoven substrate wherein the polymer comprises interpolymerized monomeric units of:
   (a) 80 to 98 wt. % of an aminoalkyl (meth)acryloyl monomer;
   (b) 2 to 20 wt. % of a poly(alkylene oxide) monomer; and
   (c) 0 to 10 wt. % of a second hydrophilic monomer.

5. The filtration medium sequence of claim 1, wherein the first filtration medium comprises a polymer grafted to the surface of a nonwoven substrate wherein the polymer comprises interpolymerized monomeric units of:
   (a) 10 to 50 wt. % of a quaternary ammonium-containing ligand monomer;
   (b) 10 to 80 wt. % of an amide monomer;
   (c) 10 to 40 wt. of an oxy monomer; and
   (d) 0 to 30 wt. % of a poly(alkylene oxide) monomer.

6. The filtration medium sequence of claim 1, wherein the functionalized microporous membrane comprises a free-radically grafted guanidyl-functional (meth)acryloyl monomer, wherein the guanidyl-functional (meth)acryloyl monomer comprises at least one of:

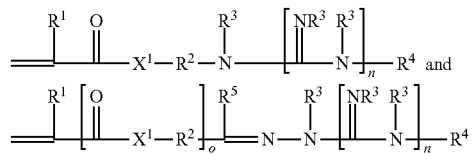

wherein
$R^1$ is H or $C_1$-$C_4$ alkyl;
$R^2$ is a (hetero)hydrocarbyl group;
each $R^3$ is independently H or hydrocarbyl;
$R^4$ is H, $C_1$-$C_{12}$ alkyl or $N(R^3)_2$;
$R^5$ is H or hydrocarbyl;
$X^1$ is —O— or —$NR^3$—;
o is 0 or 1, and
n is 1 or 2.

7. The filtration medium sequence of claim 6, wherein the free-radically grafted guanidyl-functional (meth)acryloyl monomer is grafted to a primer layer disposed on a microporous membrane, wherein the primer layer comprises a cross-linked polyamine polymer having ethylenically unsaturated polymerizable groups, wherein the cross-linked polyamine polymer having ethylenically unsaturated polymerizable groups is a reaction product of: (a) a polyamine polymer; (b) a polyfunctional crosslinking agent for the polyamine polymer; and (c) a monomer having an amine-reactive functional group and an ethylenically unsaturated polymerizable group.

8. The filtration medium sequence of claim 6, wherein the free-radically grafted guanidyl-functional (meth)acryloyl monomer is grafted on a microporous membrane in the presence of a Type II photoinitiator.

9. The filtration medium sequence of claim 1, further comprising a non-functionalized filtration medium disposed between the first filtration medium and the second filtration medium.

10. A filter device comprising
    a fluid inlet;
    a fluid outlet; and
    a filtration medium sequence fluidly connecting the fluid inlet and the fluid outlet, wherein
    the filtration medium sequence according to claim 1.

11. A method of filtration of a biological fluid, the method comprising:
    (a) providing the biological fluid, wherein the biological fluid comprises a targeted biomolecule and contaminants, and
    (b) contacting the biological fluid with the filtration medium sequence of claim 1 to obtain a filtrate.

12. The method of claim 11, wherein the targeted biomolecule is a protein.

13. The filtration medium sequence of claim 1, wherein the anion exchange nonwoven substrate has an effective fiber diameter of 1 to 6 micrometer.

14. The filtration medium sequence of claim 1, further comprising a non-functionalized filtration medium disposed between the first filtration medium and the second filtration medium.

15. The filter device of claim 10, wherein the filtration media is formed into a media cylinder comprising a plurality of pleats.

16. The filter device of claim 10, further comprising a core, wherein the second filtration medium is wound around the core and the first filtration medium is wound around second filtration medium.

17. The filter device of claim 10, wherein the filter device further comprising
- a separator element;
- an edge seal;

wherein the separator element comprises
- a central core in fluid communication with the fluid inlet;
- a first side; and
- a second side; and wherein the filter media further comprises
- a first media disk positioned on the first side of the separator element and having an outer circumferential edge and an inner circumferential edge; and
- a second media disk positioned on the second side of the separator element and having an outer circumferential edge and an inner circumferential edge; and
- wherein the outer circumferential edges of the first and second media disks are connected by the edge seal and the inner circumferential edges of the first and second media disks are connected to the central core and wherein the upstream side of the first and second media disk comprises the first filtration medium.

18. The method of claim 11, wherein the biological fluid has turbidity of at least 40 NTU.

19. The method of claim 11, wherein the biological fluid has a concentration of DNA of at least $10^5$ pg/mL.

20. The method of claim 11, wherein the biological fluid has a first host cell protein concentration and the filtrate has a second host cell protein concentration, wherein the second host cell protein concentration is at least 50% lower than the first host cell protein concentration.

* * * * *

UNITED STATES PATENT AND TRADEMARK OFFICE
CERTIFICATE OF CORRECTION

PATENT NO.      : 10,722,848 B2
APPLICATION NO. : 15/755584
DATED           : July 28, 2020
INVENTOR(S)     : Jonathan Hester et al.

Page 1 of 2

It is certified that error appears in the above-identified patent and that said Letters Patent is hereby corrected as shown below:

In the Specification

Column 5,
Lines 61 & 62, delete "chlorotrifluorocthylene" and insert -- chlorotrifluoroethylene --, therefor.
Line 62, delete "(cthylene-" and insert -- (ethylene- --, therefor.

Column 7,
Line 66, delete "monomer:" and insert -- monomer; --, therefor.

Column 8,
Line 14, delete "monomer:" and insert -- monomer; --, therefor.
Line 28, delete "$R^{L0}$" and insert -- $R^{10}$ --, therefor.

Column 10,
Line 40, delete " 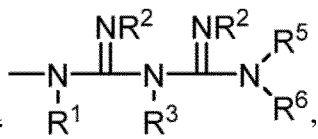 " and insert -- 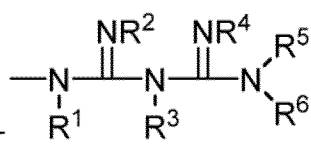 --, therefor.
Line 45, delete "-$C_2$" and insert -- -$C_{12}$ --, therefor.

Column 11,
Line 5, delete "-$NR^-$," and insert -- -$NR^3$-, --, therefor.

Column 23,
Line 5, delete "my." and insert -- $m_f$ --, therefor.
Line 6, delete "ma." and insert -- $m_i$ --, therefor.

Signed and Sealed this
Nineteenth Day of January, 2021

Andrei Iancu
*Director of the United States Patent and Trademark Office*

In the Claims

Column 31,
Line 34, in Claim 1, before "a" insert -- (i) --.
Line 66, in Claim 5, delete "wt. of" and insert -- wt. % of --, therefor.

Column 32,
Line 20, in Claim 6, delete "N($R^3$)$_2$;" and insert -- -N($R^3$)$_2$; --, therefor.